United States Patent
Takemoto

(10) Patent No.: US 8,790,327 B2
(45) Date of Patent: Jul. 29, 2014

(54) CONNECTOR AND CONNECTOR ASSEMBLY

(75) Inventor: Masafumi Takemoto, Shizuoka (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/634,089

(22) PCT Filed: Mar. 10, 2011

(86) PCT No.: PCT/JP2011/055696
§ 371 (c)(1),
(2), (4) Date: Sep. 11, 2012

(87) PCT Pub. No.: WO2011/122296
PCT Pub. Date: Oct. 6, 2011

(65) Prior Publication Data
US 2013/0006211 A1 Jan. 3, 2013

(30) Foreign Application Priority Data
Mar. 30, 2010 (JP) .................................. 2010-078884

(51) Int. Cl.
| A61J 1/14 | (2006.01) |
| A61J 1/20 | (2006.01) |
| A61J 1/10 | (2006.01) |
| A61M 5/162 | (2006.01) |
| A61M 39/00 | (2006.01) |

(52) U.S. Cl.
CPC ...... *A61J 1/2089* (2013.01); *A61J 1/14* (2013.01); *A61J 1/10* (2013.01); *A61J 2001/2048* (2013.01); *A61J 2001/2055* (2013.01); *A61J 2011/2065* (2013.01); *A61J 2001/2013* (2013.01); *A61M 5/162* (2013.01); *A61M 39/00* (2013.01)
USPC .......................................... 604/403; 604/416

(58) Field of Classification Search
CPC ............ A61J 1/2089; A61J 1/14; A61J 1/10; A61J 2001/2048; A61J 2001/2055; A61J 2001/2065; A61J 2001/2013; A61J 2001/2051; A61M 5/162; A61M 39/00; A61M 2039/00
USPC ......... 604/403, 408, 411, 412, 413, 414, 415, 604/416
See application file for complete search history.

(56) References Cited

U.S. PATENT DOCUMENTS 4,576,211 A * 3/1986 Valentini et al. ............... 141/329
4,785,858 A * 11/1988 Valentini et al. ................ 141/27
(Continued)

FOREIGN PATENT DOCUMENTS

| JP | 60-144443 | 9/1985 |
| JP | 07-148271 | 6/1995 |

(Continued)

OTHER PUBLICATIONS

U.S. Appl. No. 13/701,097 to Masafumi Takemoto, filed Nov. 30, 2012.

(Continued)

*Primary Examiner* — Adam Marcetich
(74) *Attorney, Agent, or Firm* — Greenblum & Bernstein P.L.C.

(57) ABSTRACT

A first connector is provided and includes a first connector body having a cylindrical outer tube, a cylindrical inner tube, and a hub; a hollow needle supported by the hub; a first sealing member supported by the inner tube; a coil spring that biases the hub in a proximal direction and biases the first sealing member in the distal direction; and gripping and pressing members disposed on the outer tube. A plurality of pawls are formed on a flange of the hub. A plurality of ratchet teeth are formed on an inner circumferential portion of a proximal portion of the outer tube. Each of the ratchet teeth and each of the pawls of the hub form an engagement-disengagement mechanism.

5 Claims, 17 Drawing Sheets

(56) References Cited

U.S. PATENT DOCUMENTS

| | | | |
|---|---|---|---|
| 5,122,116 A * | 6/1992 | Kriesel et al. | 604/89 |
| 5,279,597 A * | 1/1994 | Dassa et al. | 604/535 |
| 6,487,943 B1 * | 12/2002 | Jansson et al. | 81/475 |
| 6,706,031 B2 * | 3/2004 | Manera | 604/411 |
| 2002/0123736 A1 * | 9/2002 | Fowles et al. | 604/413 |
| 2002/0162712 A1 * | 11/2002 | Kauhaniemi et al. | 188/266 |
| 2004/0210207 A1 * | 10/2004 | Amisar et al. | 604/415 |
| 2005/0087645 A1 * | 4/2005 | Tracey et al. | 242/394.1 |
| 2005/0145402 A1 * | 7/2005 | Hehli et al. | 173/178 |
| 2006/0155257 A1 * | 7/2006 | Reynolds | 604/414 |
| 2008/0103485 A1 * | 5/2008 | Kruger | 604/533 |
| 2008/0172039 A1 * | 7/2008 | Raines | 604/533 |
| 2008/0205968 A1 * | 8/2008 | Malvar et al. | 401/138 |
| 2008/0277021 A1 * | 11/2008 | Horppu et al. | 141/329 |
| 2009/0104998 A1 * | 4/2009 | Chuang | 464/39 |
| 2011/0106046 A1 | 5/2011 | Hiranuma et al. | |
| 2012/0179128 A1 * | 7/2012 | Takemoto et al. | 604/414 |
| 2013/0144246 A1 * | 6/2013 | Takemoto | 604/403 |

FOREIGN PATENT DOCUMENTS

| | | |
|---|---|---|
| JP | 8-126630 | 5/1996 |
| WO | 2009/133755 | 11/2009 |

OTHER PUBLICATIONS

U.S. Appl. No. 13/700,917 to Masafumi Takemoto, filed Nov. 29, 2012.

U.S. Appl. No. 13/701,173 to Masafumi Takemoto, filed Nov. 30, 2012.

* cited by examiner

CONNECTOR AND CONNECTOR ASSEMBLY

TECHNICAL FIELD

The present invention relates to a connector and a connector assembly.

BACKGROUND ART

Ordinarily, a medicine which is dangerous when erroneously touched by a medical care staff, such as a carcinostatic agent or an immunosuppressant, is stored in a powdery state in a vial with a mouth portion sealed off by a rubber stopper.

In the case of taking the medicine out of such a vial, the following operations are carried out.

First, the mouth portion of the vial and a mouth portion of a syringe into which a dissolving liquid has been apportioned are connected to each other through a connector assembly composed of a first connector and a second connector. In this case, at an outer circumferential portion of the mouth portion of the syringe, there is provided a lock adapter formed with a screw thread at its inner circumferential surface (see, for example, Patent Document 1). At the time of connecting the syringe to a hub of the first connector, the lock adapter of the syringe is put into screw engagement with a screw engagement part formed on the hub of the first connector. As a result, the hub of the first connector and the mouth portion of the syringe are connected to each other, and the syringe is held on the hub of the first connector. Then, the first connector and the second connector connected to the mouth portion of the vial are connected to each other.

Next, the dissolving liquid is injected from the syringe into the vial via the connector assembly. Then, by a pumping operation or by shaking the vial, the medicine is uniformly dissolved in the dissolving liquid. Subsequently, the dissolving liquid with the medicine dissolved therein (hereinafter referred to as "liquid medicine") is taken out into the syringe by suction.

However, the conventional connector assembly as above-mentioned has the following problems. Since the syringe is held onto the hub of the first connector by the lock adapter, the syringe would not be disengaged even when pulled. If the syringe or the lock adapter is rotated in a direction for loosening the screw engagement, however, the syringe would be disengaged easily. If the syringe is disengaged from the hub of the first connector, the liquid medicine is scattered via the mouth portion of the syringe or the like. As a result, the liquid medicine may adhere to the medical care staff or the like, or it may be impossible to transport the liquid medicine via the connector assembly safely and assuredly.

Patent Document 1: Japanese Patent No. 3456241

DISCLOSURE OF INVENTION

It is an object of the present invention to provide a connector and a connector assembly such that a medical instrument can be prevented from being disengaged unintentionally.

In order to attain the above object, according to the present invention, there is provided a connector characterized by including:

an outer tube;

a hub disposed at a proximal portion of the outer tube so as to be movable in a direction of an axial of the outer tube and rotatable about the axis of the outer tube, relative to the outer tube, wherein the hub has a connection portion connected on a proximal side of the hub to a medical instrument having a screw engagement part and also has a projected portion for screw engagement with the screw engagement part, and at least a distal portion of the hub being inserted in the outer tube; and an engagement-disengagement mechanism provided at a joint part between the outer tube and the hub, wherein the engagement-disengagement mechanism permits rotation of the hub in both of a forward direction and a reverse direction when the hub is positioned in a first position, and inhibits the rotation of the hub in only one of the forward direction and the reverse direction when the hub is positioned in a second position on a distal side relative to the first position.

In the connector according to the present invention, preferably, the rotating direction of the hub for tightening the screw engagement between the projected portion of the hub and the screw engagement part of the medical instrument coincides with a direction in which rotation of the hub is inhibited by the engagement-disengagement mechanism.

In the connector according to the present invention, preferably, the hub has a flange at an outer circumferential portion thereof; and the engagement-disengagement mechanism has pawls provided on one of the flange and an inner circumferential portion of the outer tube, and ratchet teeth provided on the other.

In the connector according to the present invention, preferably, the connector further includes biasing means for biasing the hub in a proximal direction; and the hub is positioned in the first position by a biasing force of the biasing means, and, when the hub is moved in a distal direction from the first position against the biasing force of the biasing means to be positioned in the second position, the rotation of the hub in only one of the forward direction and the reverse direction is inhibited by the engagement-disengagement mechanism.

In addition, in order to attain the above object, according to the present invention, there is provided a connector assembly characterized by including:

the connector according to the present invention; and a mating connector connected to the connector and having on a distal side a connection portion to which to connect a liquid storing vessel capable of storing a liquid.

In the connector according to the present invention, preferably, the pawls and the ratchet teeth are respectively provided in plurality along a circumferential direction.

In the connector according to the present invention, preferably, the projected portion is a screw thread or flange-shaped projection.

In the connector according to the present invention, preferably, the connector includes:

a hollow needle which is provided inside the outer tube so as to communicate with the connection portion and has an opening portion opening at a distal portion thereof;

a sealing member which is disposed to be movable relative to the outer tube in the direction of the axis of the outer tube, has a to-be-pierced section capable of being pierced by the hollow needle, seals off a lumen portion of the outer tube, and is formed of an elastic material; and to-be-pierced section biasing means for biasing the to-be-pierced section in the distal direction, wherein the above-mentioned biasing means serves also as the to-be-pierced section biasing means.

In the connector according to the present invention, preferably, the biasing means is a coil spring disposed around the hollow needle.

In the connector according to the present invention, preferably, the medical instrument has a syringe having a mouth portion at a distal portion thereof; and the connector has the connection portion to which to connect the mouth portion of the syringe.

In the connector according to the present invention, preferably, a lock adapter having the screw engagement part at an inner circumferential surface thereof, wherein the lock adapter is provided at an outer circumferential portion of the mouth portion of the syringe; and when the projected portion and the screw engagement part are put into screw engagement with each other, a portion of the hub which protrudes from the proximal end of the outer tube is housed in the lock adapter.

BRIEF DESCRIPTION OF DRAWINGS

FIG. 1 is an exploded perspective view showing an embodiment of a connector assembly according to the present invention.
FIG. 2 is a longitudinal sectional view (partly side view) showing a process until a first connector and a second connector in the connector assembly shown in FIG. 1 are brought into an assembled state.
FIG. 3 is a longitudinal sectional view showing the process until the first connector and the second connector in the connector assembly shown in FIG. 1 are brought into the assembled state.
FIG. 4 is a longitudinal sectional view showing the process until the first connector and the second connector in the connector assembly shown in FIG. 1 are brought into the assembled state.
FIG. 5 is a longitudinal sectional view showing the process until the first connector and the second connector in the connector assembly shown in FIG. 1 are brought into the assembled state.
FIG. 6 is a perspective view (a view corresponding to FIG. 2) showing the process until the first connector and the second connector in the connector assembly shown in FIG. 1 are brought into the assembled state.
FIG. 7 is a perspective view (a view corresponding to FIG. 3) showing the process until the first connector and the second connector in the connector assembly shown in FIG. 1 are brought into the assembled state.
FIG. 8 is a perspective view (a view corresponding to FIG. 4) showing the process until the first connector and the second connector in the connector assembly shown in FIG. 1 are brought into the assembled state.
FIG. 9 is a perspective view (a view corresponding to FIG. 5) showing the process until the first connector and the second connector in the connector assembly shown in FIG. 1 are brought into the assembled state.
FIG. 10 is a sectional view taken along line A-A of FIG. 3.
FIG. 11 is a sectional view taken along line B-B of FIG. 4.
FIG. 12 is a longitudinal sectional view (partly side view) showing the vicinity of a proximal portion of the first connector in the connector assembly shown in FIG. 2.

FIG. 13 is a longitudinal sectional view (partly side view) showing the vicinity of the proximal portion of the first connector in the connector assembly shown in FIG. 2.
FIG. 14 is a perspective view showing an outer tube of the first connector in the connector assembly shown in FIG. 1.
FIG. 15 is a perspective view showing a hub of the first connector in the connector assembly shown in FIG. 1.
FIG. 16 is a partially longitudinal sectional view showing a syringe which is connected to the first connector in the connector assembly shown in FIG. 1.
FIG. 17 is a longitudinal sectional view of a bag which is connected to the second connector in the connector assembly shown in FIG. 1.

MODE FOR CARRYING OUT THE INVENTION

Now, a connector and a connector assembly according to the present invention will be described in detail below, based on a preferred embodiment shown in the attached drawings.

Figure 1:
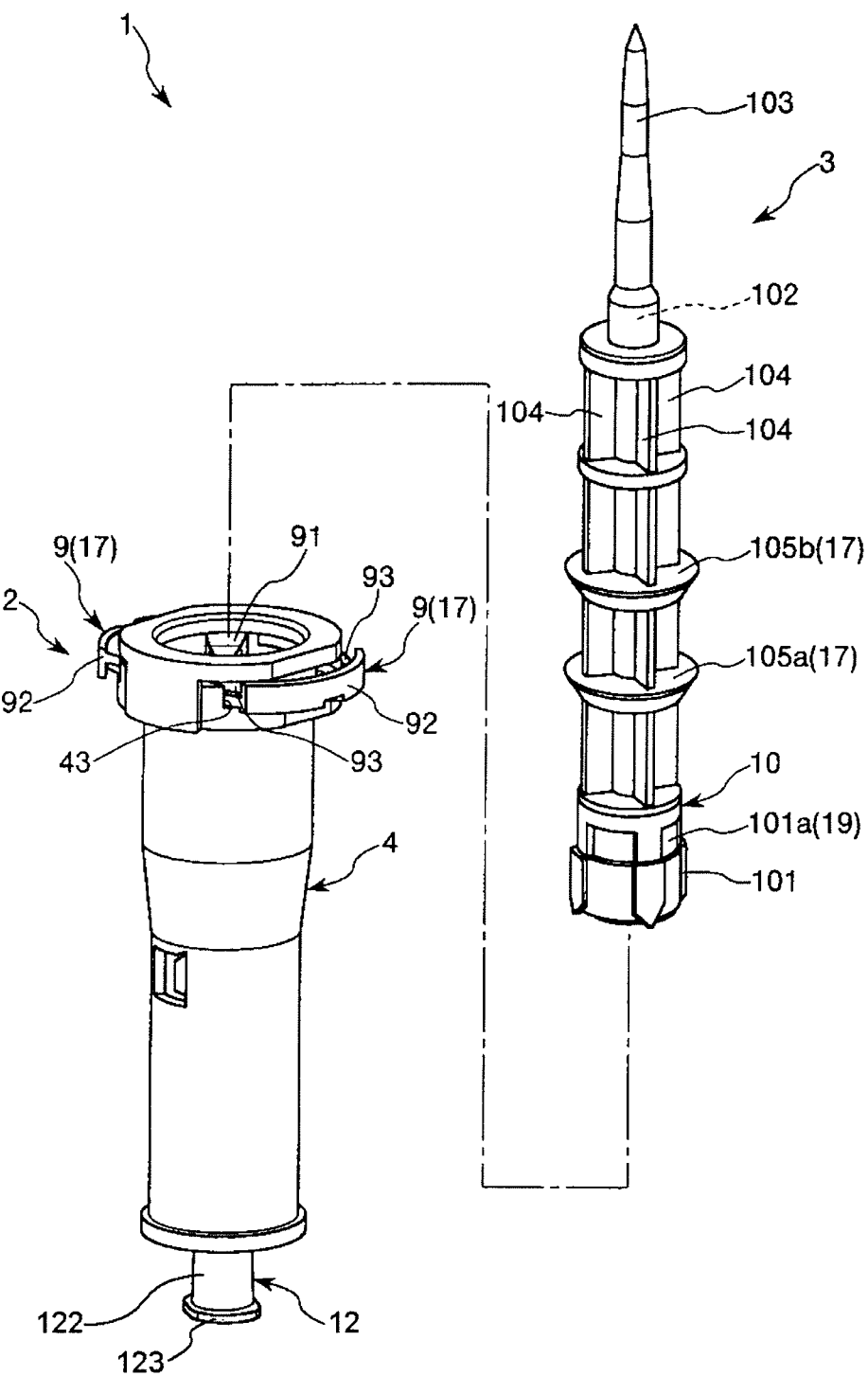
[FIG. 1]
Figure 10:
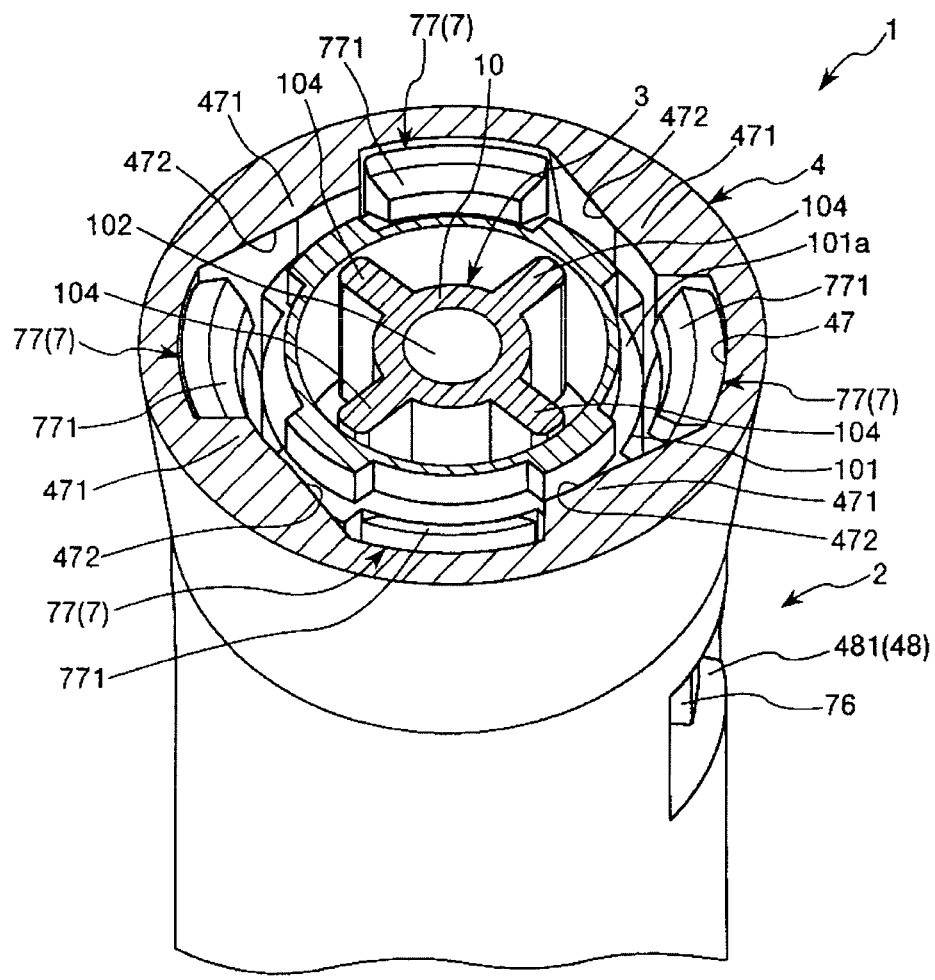
[FIG. 10]
Figure 11:
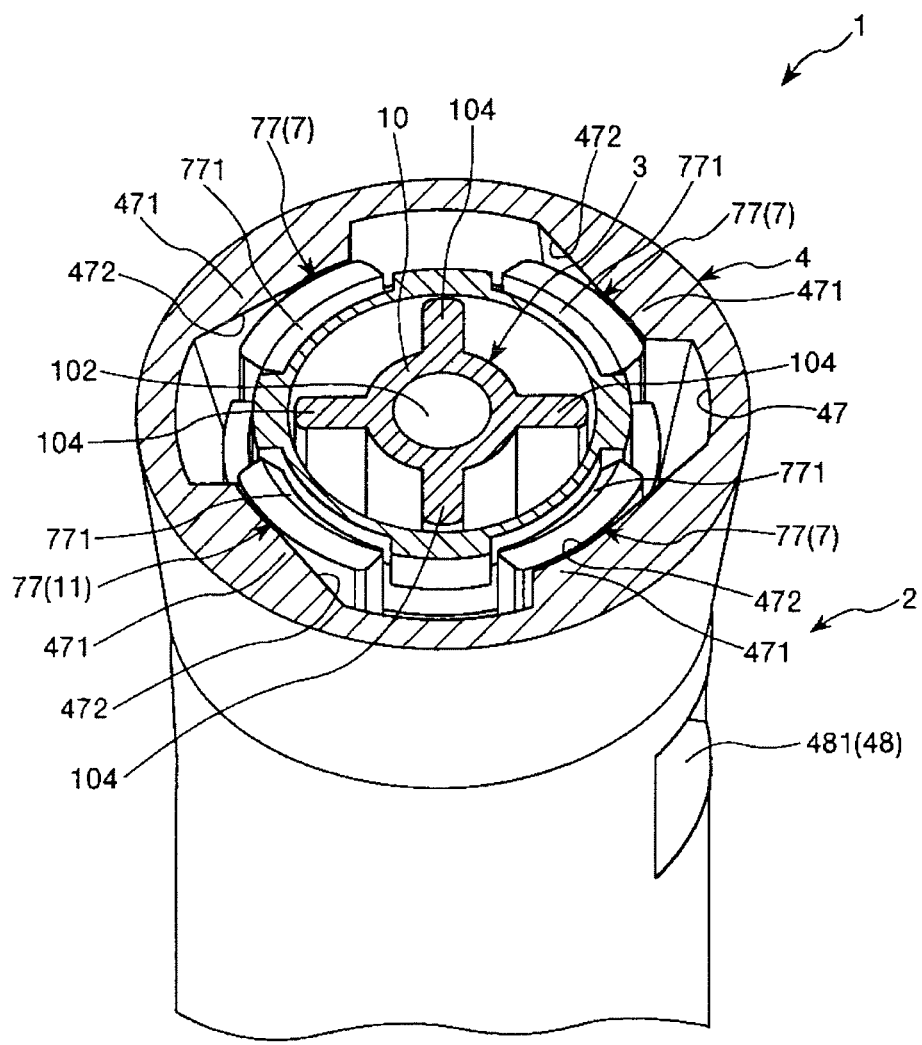
[FIG. 11]
Figure 12:
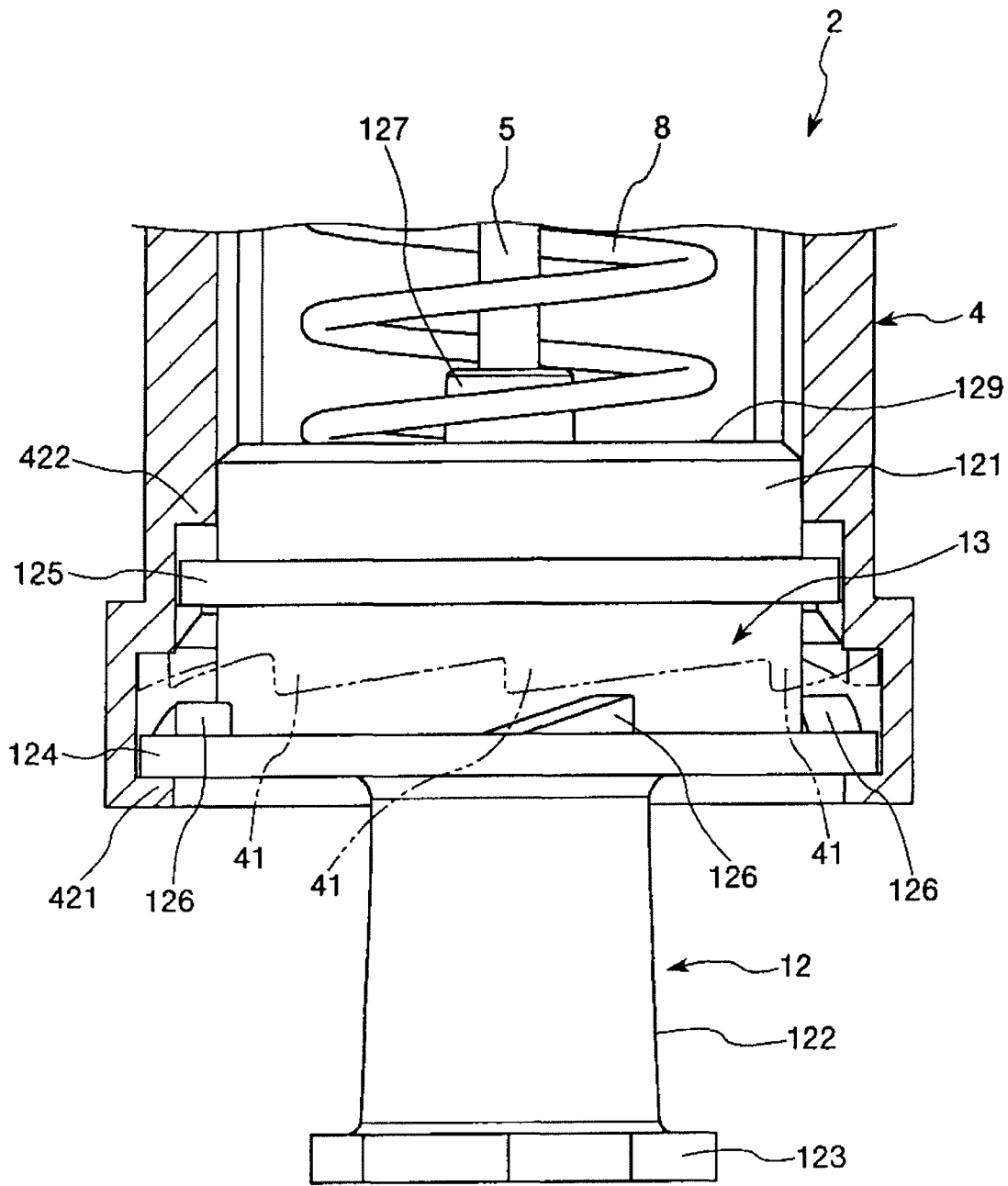
[FIG. 12]
Figure 13:
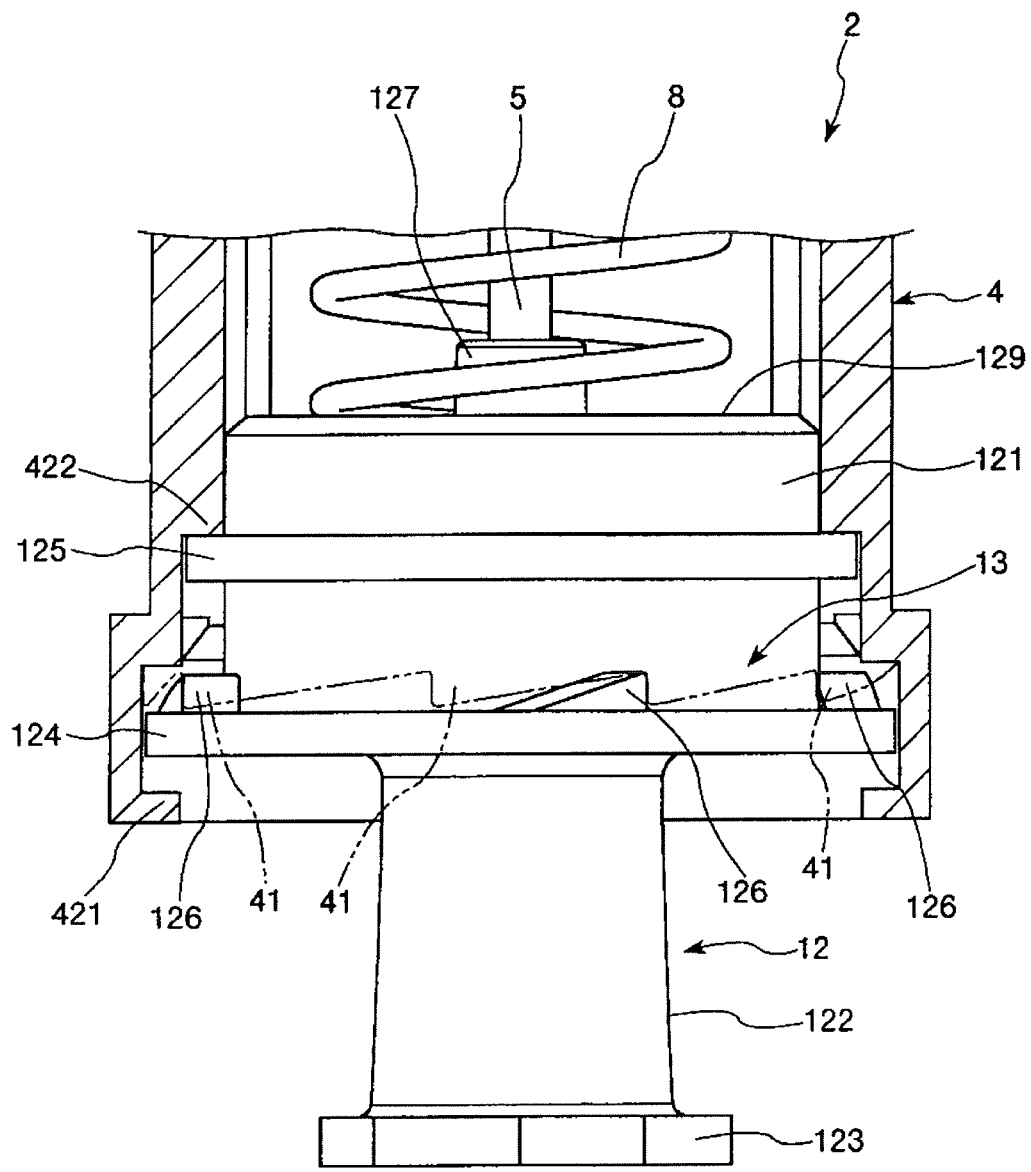
[FIG. 13]
Figure 14:
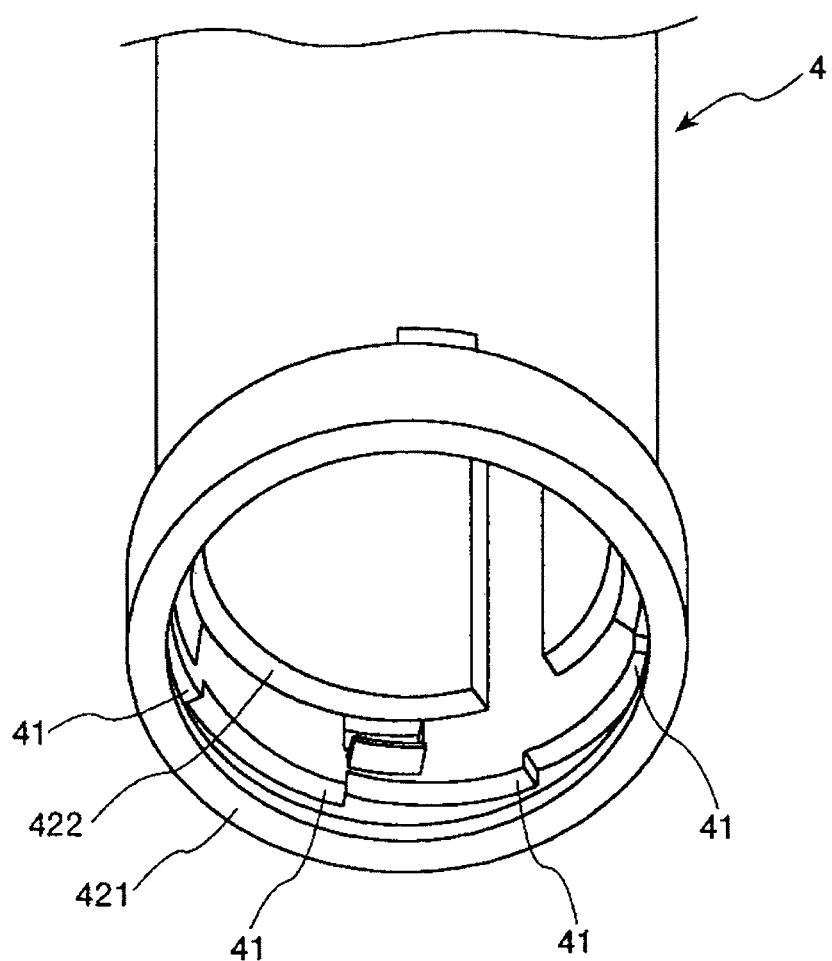
[FIG. 14]
Figure 15:
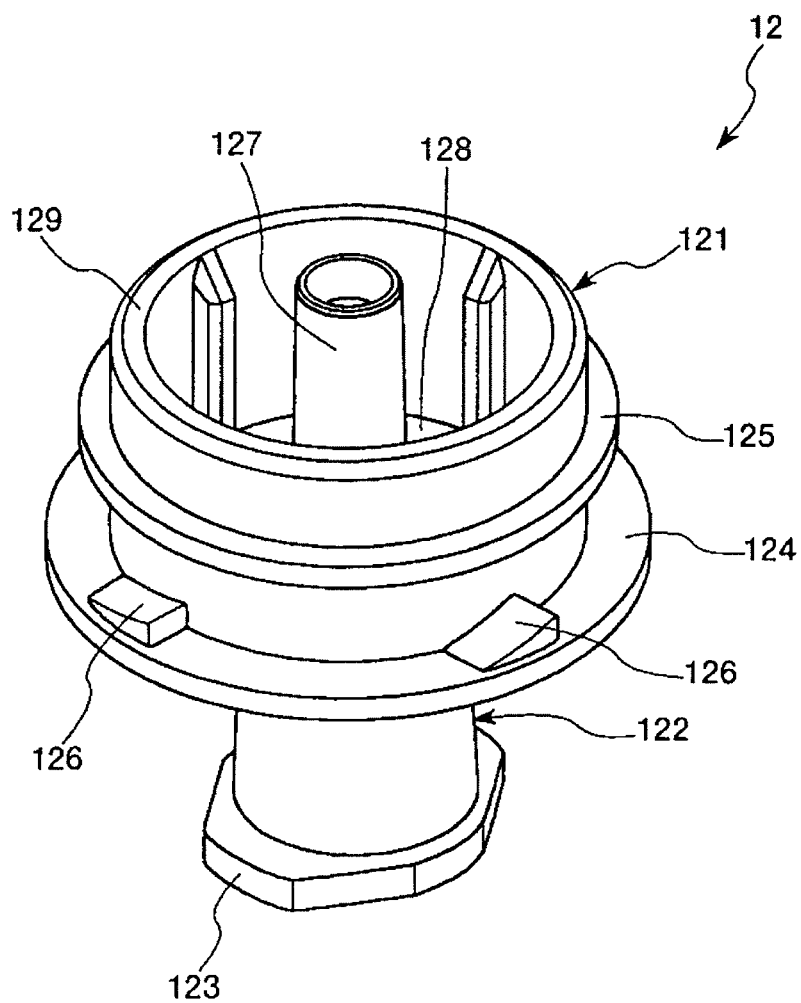
[FIG. 15]
Figure 16:
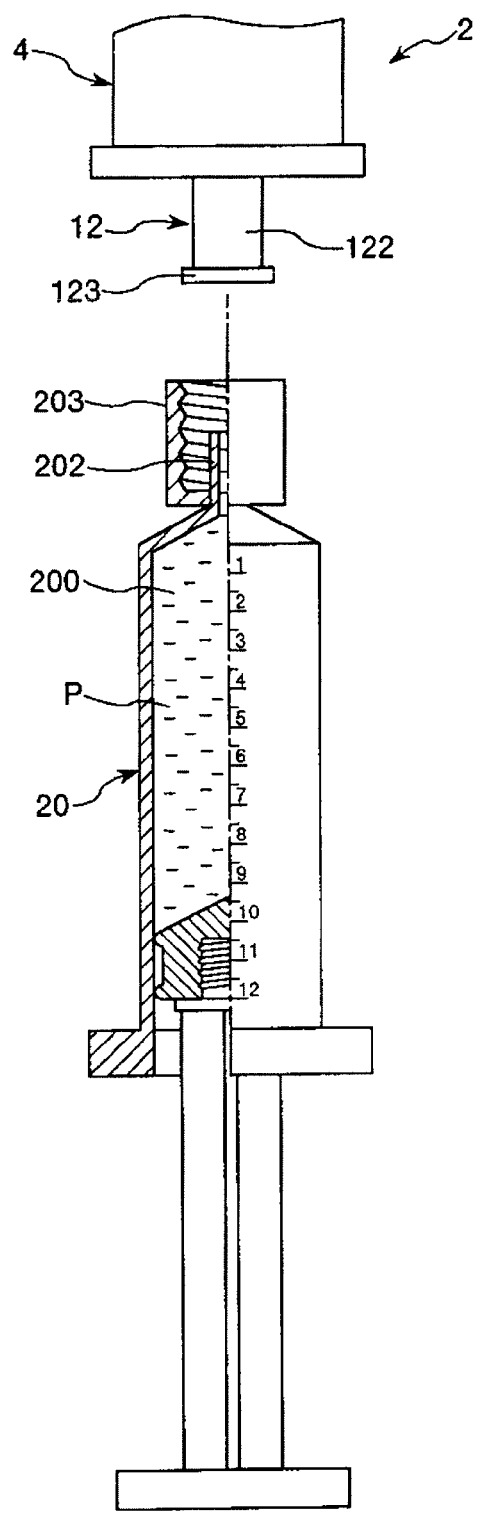
[Fig. 16]
Figure 17:
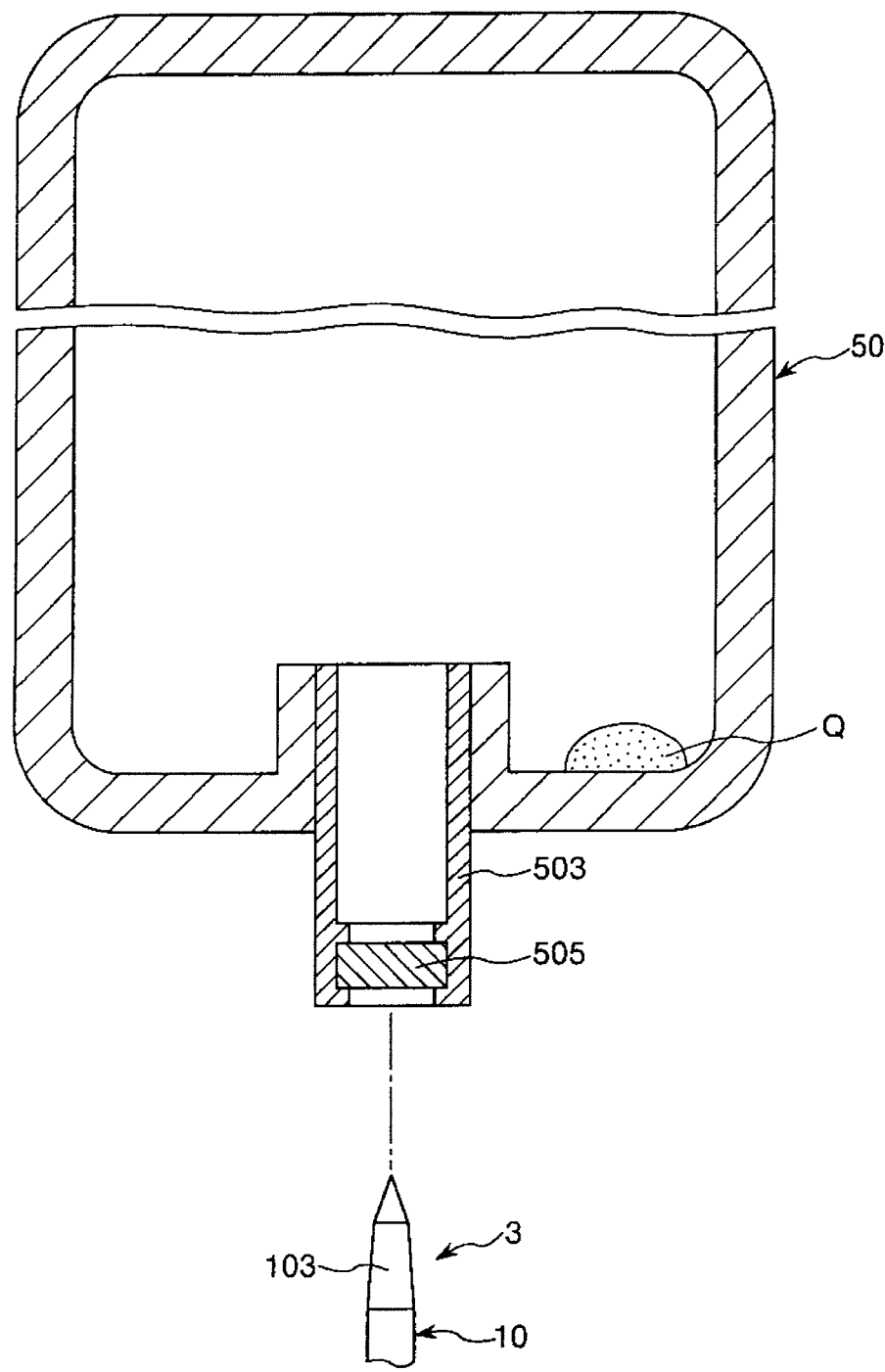
[FIG. 17]

FIG. 1 is an exploded perspective view showing an embodiment of the connector assembly according to the present invention; FIGS. 2 to 5 are respectively longitudinal sectional views showing a process until a first connector and a second connector in the connector assembly shown in FIG. 1 are brought into an assembled state; FIGS. 6 to 9 are perspective views (views corresponding to FIGS. 2 to 5, respectively) showing the process until the first connector and the second connector in the connector assembly shown in FIG. 1 are brought into the assembled state; FIG. 10 is a sectional view taken along line A-A of FIG. 3; FIG. 11 is a sectional view taken along line B-B of FIG. 4; FIGS. 12 and 13 are longitudinal sectional views (partly side views) showing the vicinity of a proximal portion of the first connector in the connector assembly shown in FIG. 2; FIG. 14 is a perspective view showing an outer tube of the first connector in the connector assembly shown in FIG. 1; FIG. 15 is a perspective view showing a hub of the first connector in the connector assembly shown in FIG. 1; FIG. 16 is a partly longitudinal sectional view showing a syringe which is connected to the first connector in the connector assembly shown in FIG. 1; and FIG. 17 is a longitudinal sectional view of a bag which is connected to the second connector in the connector assembly shown in FIG. 1. Incidentally, in the following, the upper side in FIGS. 1 to 17 will be referred to as "distal (end)" or "upper" or "upper side," and the lower side as "proximal (end)" or "lower" or "lower side," for convenience of description.

As shown in FIGS. 1 to 15, a connector assembly 1 includes a first connector (female connector) 2 and a second connector (male connector) 3. As shown in FIG. 16, the first connector 2 is mounted to a syringe (first medical instrument) 20. As shown in FIG. 17, the second connector 3 is mounted to a bag (second medical instrument) 50. The connector assembly 1 is used, in an assembled state (a state shown in FIGS. 5 and 9) in which the first connector 2 and the second connector 3 have been assembled by inserting the second connector 3 into the first connector 2 from a distal side of the latter, for feeding a liquid from a first connector 2 side toward a second connector 3 side or in a reverse direction thereof.

As shown in FIG. 17, the bag 50 is for storing a powdery drug Q. The bag 50 is provided at a proximal portion thereof with a mouth portion 503 composed of a hard pipe. A liquid can be fed in and out through the mouth portion 503.

In addition, a rubber stopper 505 for sealing off the mouth portion 503 is mounted to the mouth portion 503. The rubber stopper 505 is pierced by a bottle needle portion 103 of the second connector 3. In this pierced state, the second connector 3 and the bag 50 communicate with each other.

The drug Q stored in the bag 50 is not particularly restricted. Examples of the drug Q include drugs which are dangerous when erroneously touched by medical care staffs, such as carcinostatic agents, an immunosuppressant, and etc., drugs which need dissolution when put to use, such as antibiotic, blood coagulant, and etc., drugs which need dilution, such as drugs for children, and etc., and drugs which are apportioned multiple times, such as vaccine, heparin, drugs for children, and etc. Besides, the drug Q is not limited to powdery ones; for example, the drug Q may be liquid.

In addition, as shown in FIG. 16, a lock adapter 203 is provided at an outer circumferential portion of a mouth portion 202 provided at a distal portion of the syringe 20. The lock adapter 203 is provided at an inner circumferential surface thereof with a screw thread as a screw engagement part for screw engagement with a projection 123 of a hub portion 122. In this embodiment, the lock adapter 203 is fixed to the mouth portion 202.

At the time of connecting the syringe 20 to the hub portion 122 of a hub 12 of the first connector 2, the mouth portion 202 of the syringe 20 is inserted into a proximal portion of the hub portion 122 of the hub 12 (described later) of the first connector 2, the lock adapter 203 is rotated together with the syringe 20, and the screw thread formed at the inner circumferential surface of the lock adapter 203 is thereby screw engaged with the projection 123 formed at the hub portion 122. Hereinafter, the screw engagement between the projection 123 and the screw thread of the lock adapter 203 will also be referred to simply as "screw engagement between the projection 123 and the lock adapter 203." As a result, the hub portion 122 of the hub 12 and the mouth portion 202 of the syringe 20 are connected to each other, and the projection 123 and the lock adapter 203 are screw engaged with each other, whereby the syringe 20 is held on the hub 12. Incidentally, in this state, a portion of the hub 12 which is protruding from the proximal end of the outer tube 4, namely the hub portion 122, is housed in the lock adapter 203.

Incidentally, while the lock adapter 203 is fixed to the mouth portion 202 in this embodiment, this is not restrictive; for example, the lock adapter 203 may be one which is disposed to be movable relatively to the mouth portion 202 along an axial direction of the syringe 20, one which is rotatable relatively to the mouth portion 202 about an axis (concentrically), or one which is movable along the axial direction and rotatable about the axis relatively to the mouth portion 202.

Now, the connector assembly 1 will be described below. As above-mentioned, the connector assembly 1 has the first connector 2 and the second connector 3.

As shown in FIGS. 2 to 5 and FIGS. 12 to 15, the first connector 2 includes: a first connector body having a cylindrical outer tube 4, a cylindrical inner tube 7, and the hub 12; a hollow needle 5 supported on the hub 12; a first sealing member 6 supported on the inner tube 7; a coil spring 8 which serves as biasing means for biasing the hub 12 in the proximal direction and as to-be-pierced section biasing means for biasing the first sealing member 6 in the distal direction; and gripping and pressing members 9 disposed on the outer tube 4. Incidentally, since the coil spring 8 is made to serve as the two means, a number of component parts can be reduced and a simplified structure is ensured.

As shown in FIGS. 1, 2 and 12 to 14, the outer tube 4 is tubular in shape. The second connector 3 is inserted into the outer tube 4 via a distal opening of the outer tube 4, whereby the first connector 2 and the second connector 3 are interconnected.

The outer tube 4 is formed, at an inner circumferential portion of a proximal portion thereof, with a plurality of (in the configuration shown, eight) ratchet teeth 41 projecting in the proximal direction. The ratchet teeth 41 are arranged at equiangular intervals along a circumferential direction. In addition, the ratchet teeth 41 each extend along the circumferential direction.

Besides, the inner circumferential portion of the outer tube 4 is provided with a stepped portion 422 on the distal side of the ratchet teeth 41. In addition, the inner circumferential portion of the outer tube 4 is formed with an annular rib 421 at the proximal end thereof.

As shown in FIGS. 1, 2, 12 and 13, the hub 12 is disposed at the proximal portion of the outer tube 4 so as to be movable relative to the outer tube 4 in the axial direction of the outer tube 4 and to be rotatable relative to the outer tube 4 about the axis of the outer tube 4.

As shown in FIGS. 1, 2, 12, 13 and 15, the hub 12 has a bottomed tubular main body portion 121, and the hub portion (first connection portion) 122 having a tubular shape and projecting in the proximal direction from a central portion of a bottom portion 128 of the main body portion 121. The main body portion 121 and the hub portion 122 are disposed concentrically. At least a distal portion of the hub 12, namely the main body portion 121, is inserted in the outer tube 4.

A flange-shaped projection (projected portion) 123 is formed at an outer circumferential portion of the proximal end of the hub portion 122. The shape of the projection 123 is non-circular as viewed along the axial direction of the hub portion 122, and is such a shape that the length of the projection 123 in one of two directions orthogonal to each other is greater than that in the other of the two directions. The projection 123 is a part for screw engagement with the screw thread formed on the lock adapter 203 of the syringe 20 which will be described later. Incidentally, the projection 123 is not restricted to the above-mentioned projection 123, insofar as it can make screw engagement with the screw thread formed on the lock adapter 203; for example, the projection 123 may be a screw thread or the like.

At a central portion of the bottom portion 128 of the main body portion 121, a tubular strut 127 is formed to project in the distal direction. The main body portion 121 and the strut 127 are disposed concentrically with each other.

The hollow needle 5 is inserted in the strut 127, and a proximal portion of the hollow needle 5 is fixed to the bottom portion 128. In other words, the hollow needle 5 is supported by the hub 12. In addition, the bottom portion 128 is formed with an opening (not shown) at a position corresponding to a lumen (first flow channel 52) of the hollow needle 5, whereby the hub portion 122 and the hollow needle 5 are made to communicate with each other.

Besides, as above-mentioned, with the projection 123 of the hub portion 122 and the lock adapter 203 of the syringe 20 put into screw engagement with each other, the first connector 2 is mounted to the syringe 20, and, in this mounted state, the first connector 2 can be used (see FIG. 16). In the mounted state, further, a space 200 in the syringe 20 and the lumen (first flow channel 52) of the hollow needle 5 are made to communicate with each other through the hub portion 122. This makes it possible to supply a dissolving liquid P from the syringe 20 into the hollow needle 5.

In addition, at an outer circumferential portion of the main body portion 121, a pair of flanges 124 and 125 is formed to be spaced from each other by a predetermined distance along the axial direction. The flange 124 is disposed at the proximal end of the main body portion 121, while the flange 125 is disposed on the distal side of the flange 124. Besides, the axial distance between a proximal-side surface of the flange 124 and a distal-side surface of the flange 125 is set to be shorter than the axial distance between the rib 421 and the stepped portion 422 of the outer tube 4.

In addition, the flange 124 is located on the distal side of the rib 421 of the outer tube 4, while the flange 125 is located on the proximal side of the stepped portion 422 of the outer tube 4. This ensures that a range of axial movement of the hub 12 relative to the outer tube 4 is restricted. In other words, the hub 12 can be moved to a position where the flange 124 is in contact with the rib 421 of the outer tube 4 (a first position shown in FIG. 12) and a position where the flange 125 is in contact with the stepped portion 422 of the outer tube 4 (a second position shown in FIG. 13). Therefore, the flanges 124 and 125 constitute movement range restricting means for restricting the range of axial movement of the hub 12 relative to the outer tube 4. Incidentally, the second position is located on the distal side relative to the first position.

Besides, the flange 124 is provided at a distal-side surface thereof with a plurality of (in the configuration shown, four) pawls 126 projecting in the distal direction. The pawls 126 are disposed at positions corresponding to the ratchet teeth 41 of the outer tube 4, at equiangular intervals along the circumferential direction. The pawls 126 and the ratchet teeth 41 of the outer tube 4 constitute an engagement-disengagement mechanism 13 provided at a joint part between the outer tube 4 and the hub 12.

When the hub 12 is positioned in the first position shown in FIG. 12, the pawls 126 of the hub 12 are located on the proximal side relative to the ratchet teeth 41 of the outer tube 4, whereby the hub 12 is permitted to be rotated in a forward direction and in a reverse direction.

On the other hand, when the hub 12 is positioned in the second position shown in FIG. 13, the pawls 126 of the hub 12 are located at such positions that they can be engaged with the ratchet teeth 41 of the outer tube 4, whereby rotation of the hub 12 in only one of the forward direction and the reverse direction is inhibited. In this case, a rotating direction of the hub 12 in which the screw engagement between the projection 123 of the hub 12 and the lock adapter 203 of the syringe 20 is tightened coincides with the direction in which the rotation of the hub 12 is inhibited by the engagement-disengagement mechanism 13. Incidentally, in the following description, the rotating direction of the hub 12 in which the screw engagement between the projection 123 of the hub 12 and the lock adapter 203 of the syringe 20 is tightened will also be referred to simply as "a screw engagement tightening direction".

As a result, with the hub 12 positioned in the second position, the rotation of the hub 12 in the screw engagement tightening direction is inhibited. In addition, when the mouth portion 202 of the syringe 20 is inserted into the proximal portion of the hub portion 122 and the lock adapter 203 is rotated together with the syringe 20, the lock adapter 203 comes into screw engagement with the projection 123 of the hub portion 122, whereby the syringe 20 is mounted to the hub portion 122.

After the syringe 20 is mounted to the hub portion 122, the syringe 20 cannot be detached from the hub portion 122, even if the hub 12 is positioned in either the first position or the second position. More specifically, when the hub 12 is positioned in the first position, the hub 12 can be rotated in the forward direction and in the reverse direction, so that the screw engagement between the projection 123 of the hub portion 122 and the lock adapter 203 cannot be loosened. Besides, when the hub 12 is positioned in the second position, only the rotation of the hub 12 in the screw engagement tightening direction is inhibited, so that, again, the screw engagement between the projection 123 of the hub portion 122 and the lock adapter 203 cannot be loosened.

In addition, as shown in FIGS. 6 to 9, a wall portion of the outer tube 4 is formed in an intermediate portion thereof with a groove portion 48 penetrating the wall portion. The groove portion 48 is in the shape of a letter "L" in side view. The groove portion 48 is composed of a transverse groove 481 formed along the circumferential direction of the wall portion of the outer tube 4, and a longitudinal groove 482 formed to extend in the proximal direction from one end of the transverse direction 481 along the axial direction of the outer tube 4. A projected portion 76 of the inner tube 7 is inserted in the groove portion 48. Besides, the projected portion 76 of the inner tube 7 can be moved within the groove portion 48.

As shown in FIGS. 2 to 5, the wall portion of the outer tube 4 is formed at a distal portion thereof with a pair of groove portions 43 on opposite sides of the center axis thereof. In the groove portions 43, two annular gripping and pressing members 9 are inserted in a mutually overlapping state. The gripping and pressing members 9 function as a part of a stopper 17 for restricting distal movement of the second connector 3 (second connector body 10) in the outer tube 4. As a configuration of the stopper 17, a known configuration (for example, the configuration of "the hub engagement-disengagement mechanism" described in Japanese Patent Laid-open No. Hei 8-126630) can be used.

In this case, the gripping and pressing members 9 are each provided at a part of an outer circumferential portion thereof with an operating part 92 for operation to press the gripping and pressing member 9. With the operating part 92 pressed, the gripping and pressing member 9 is moved in a direction orthogonal to the axis of the outer tube 4.

In addition, the gripping and pressing members 9 are each provided, at a part thereof on the opposite side from the operating part 92, with a plurality of projected portions (first engagement portions) 91 projecting toward the inside. Besides, the projected portion 91 of the gripping and pressing member 9 on one side and the projected portion 91 of the gripping and pressing member 9 on the other side are located to be opposed to each other, with the center axis of the outer tube 4 therebetween.

Furthermore, each of the gripping and pressing members 9 is provided, on the same side as the projected portion 91, with a pair of elastic pieces 93 projecting from the outer circumferential portion thereof. The elastic pieces 93 of the gripping and pressing member 9 on one side are set in contact with the inside of the operating part 92 of the gripping and pressing member 9 on the other side, and, similarly, the elastic pieces 93 of the gripping and pressing member 9 on the other side are set in contact with the inside of the operating part 92 of the gripping and pressing member 9 on the one side.

At the time of operating to press each of the gripping and pressing members 9, the pressing operation is conducted against the biasing force (elastic force) of the elastic pieces 93. This operation results in that the projected portion 91 of the gripping and pressing member 9 on one side and the projected portion 91 of the gripping and pressing member 9 on the other side are spaced apart from each other. When the pressing force on each of the gripping and pressing members 9 is removed, the biasing force of the elastic pieces 93 bring the projected portion 91 of the gripping and pressing member 9 on the one side and the projected portion 91 of the gripping and pressing member 9 on the other side into a mutually close state.

Figure 3:
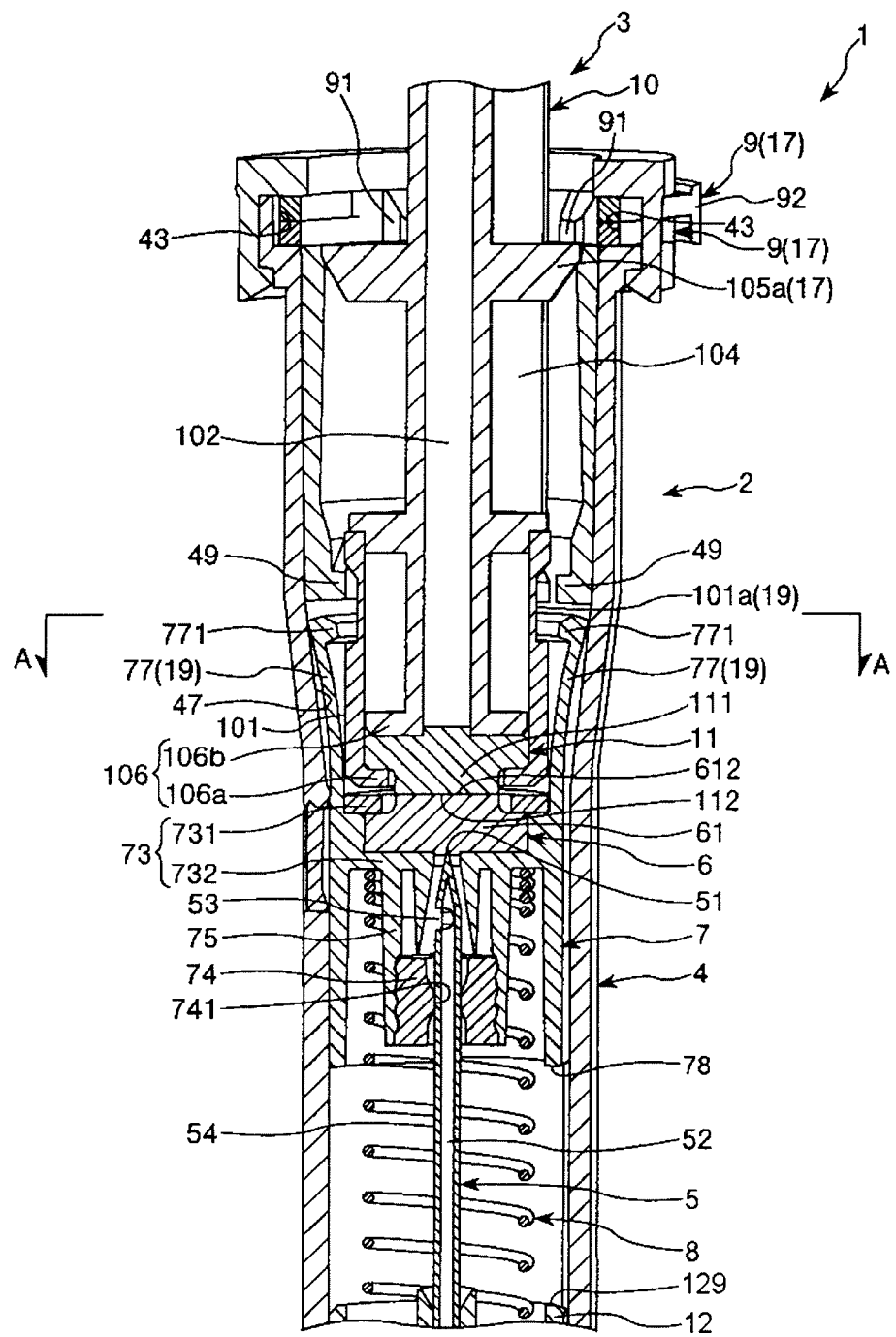
[FIG. 3]
Figure 4:
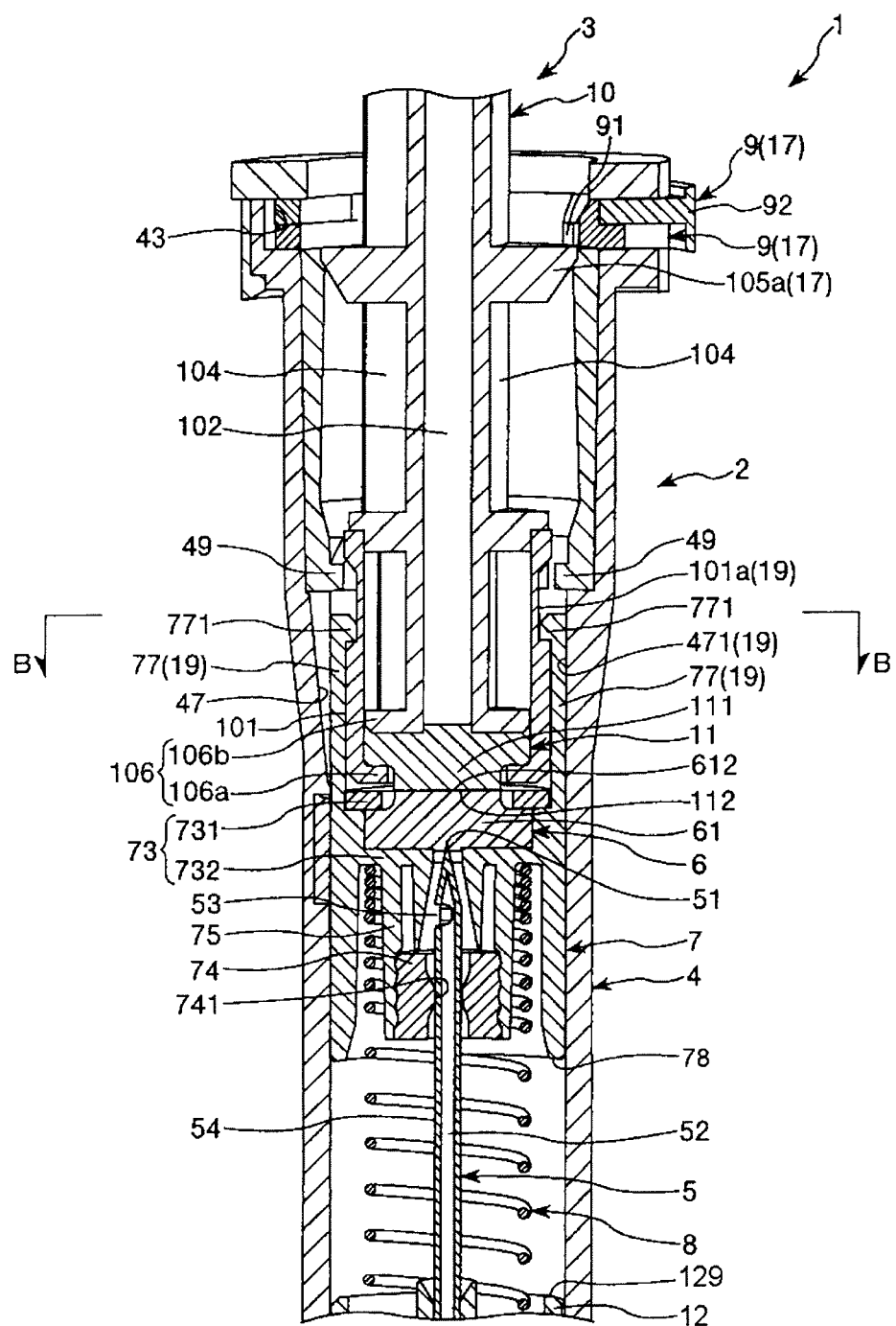
[FIG. 4]
Figure 5:
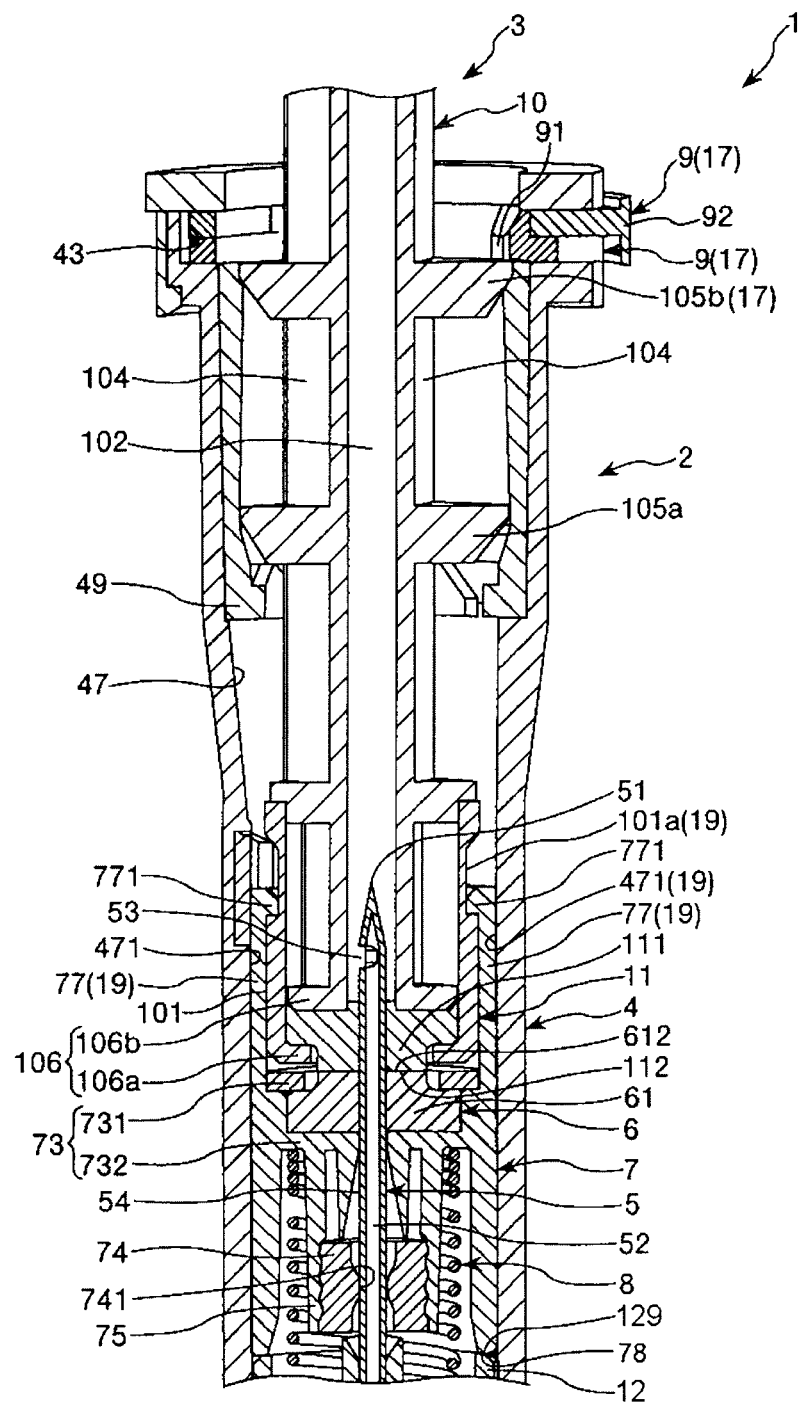
[FIG. 5]

When the projected portion 91 of the gripping and pressing member 9 on one side and the projected portion 91 of the gripping and pressing member 9 on the other side are in the mutually close state, the projected portions 91 are as a whole engaged with an engagement portion (second engagement portion) 105a or 105b of the second connector 3 (see FIGS. 3 to 5). This makes it possible to assuredly prevent the second connector 3 from being disengaged from the outer tube 4 in an unwilling manner.

In addition, when the projected portion 91 of the gripping and pressing member 9 on one side and the projected portion 91 of the gripping and pressing member 9 on the other side are in a mutually spaced apart state, the gripping and pressing members 9 and the second connector 3 are disengaged from each other.

As shown in FIG. 1, the engagement portions 105a and 105b of the second connector 3 are each composed of a flange portion which is formed at the outer circumferential portion of the second connector body 10 and has an enlarged outside diameter. The engagement portions 105a and 105b are spaced from each other along the axial direction of the second connector body 10. Besides, as shown in FIGS. 3 and 5, according to the depth of insertion of the second connector 3 into the first connector, one of the engagement portions 105a and 105b is engaged with the projected portions 91, as above-mentioned.

In the connector assembly 1, the gripping and pressing members 9 and the engagement portions 105a and 105b of the second connector 3 constitute "the stopper 17" by which the outer tube 4 and the second connector 3 are locked together.

Figure 2:
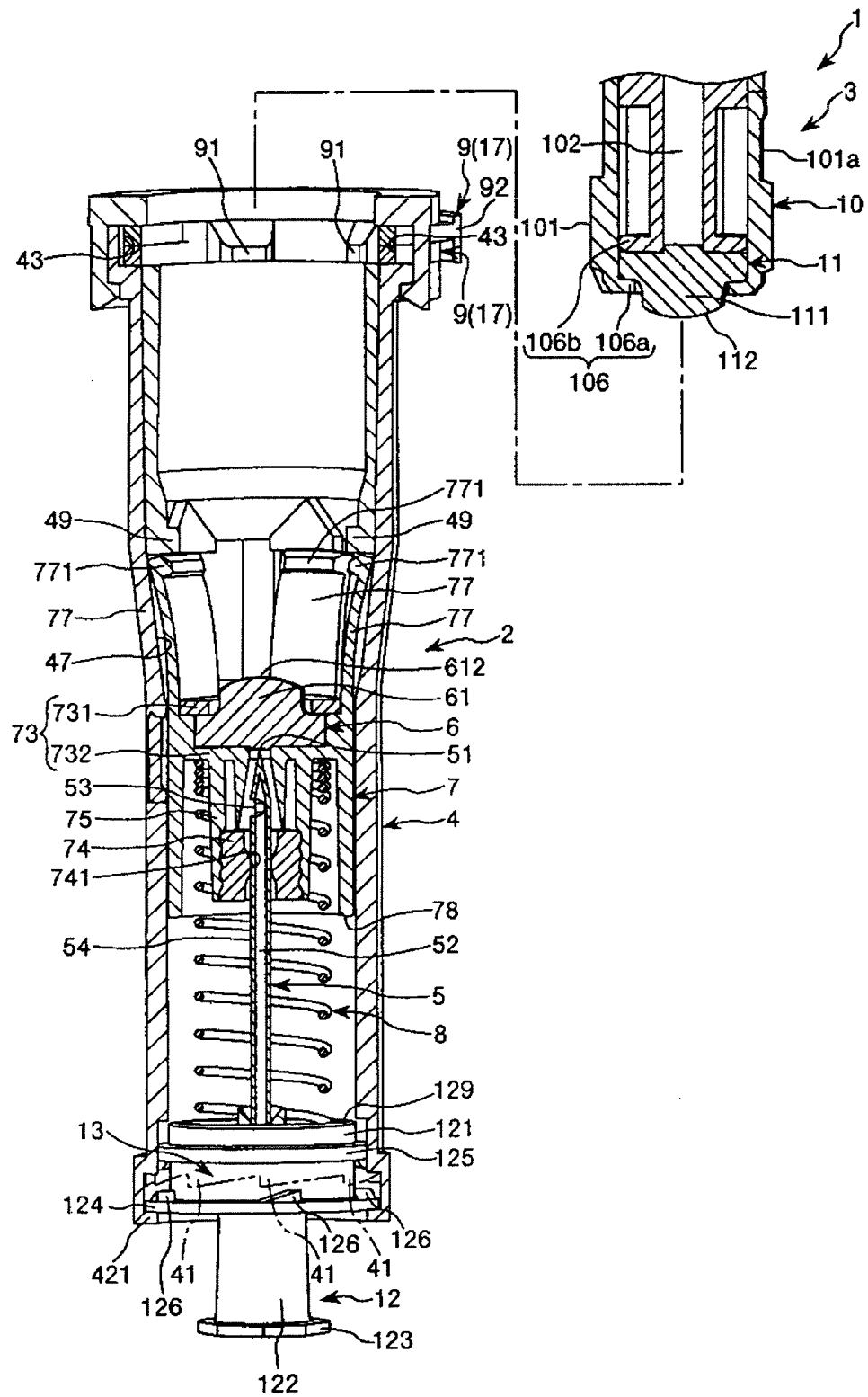
[FIG. 2]
Figure 6:
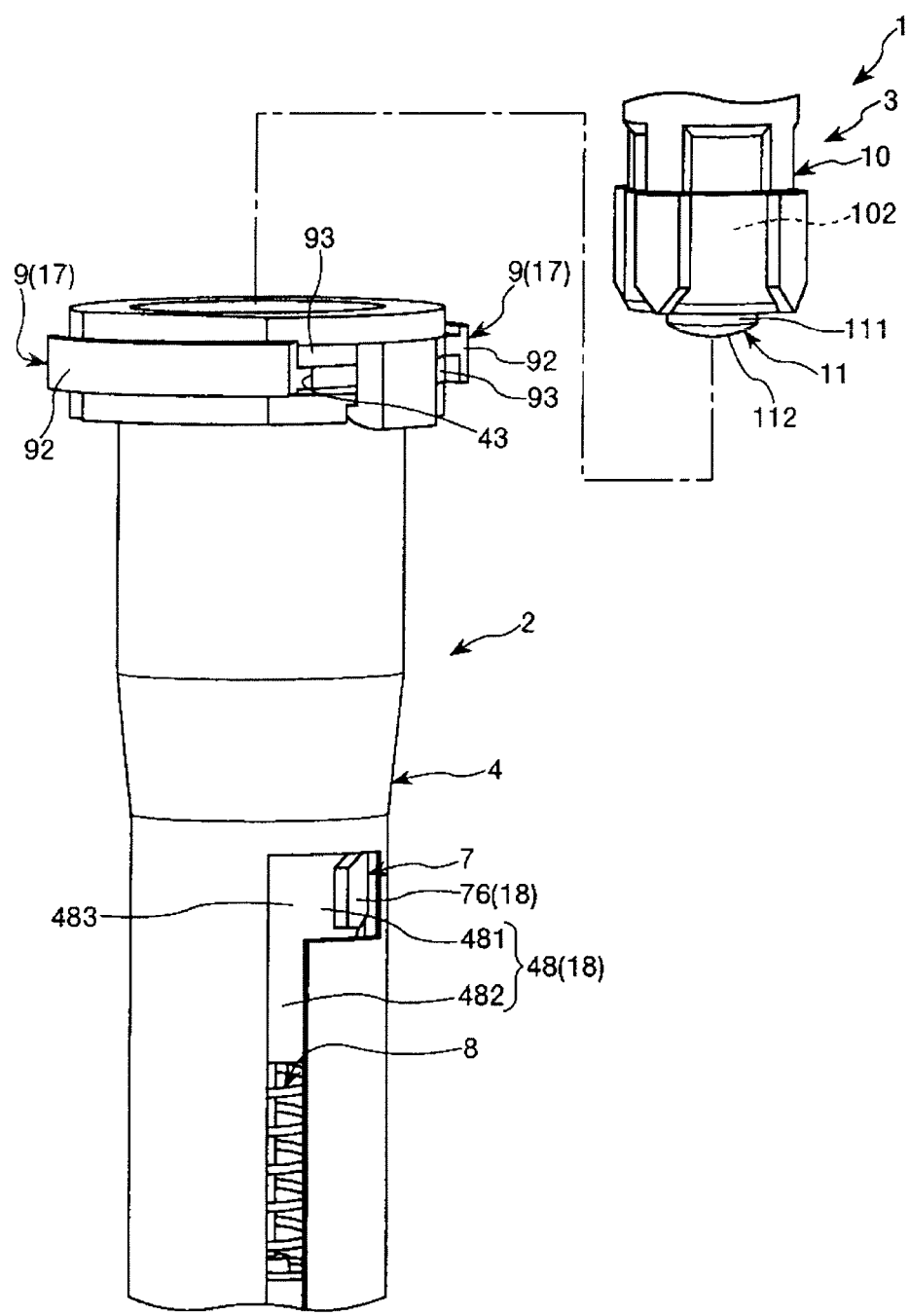
[FIG. 6]

As shown in FIGS. 2 and 6, the wall portion of the outer tube 4 is formed, at a portion between the groove portion 48 and the groove portion 43 of an inner circumferential portion 47 thereof, with a plurality of (in this embodiment, four) stepped portions 49 projecting toward the inside. As shown in FIG. 2, with the inner tube 7 making contact with each of the stepped portions 49, distal movement of the inner tube 7 can be restrained, and, accordingly, disengagement of the inner tube 7 from the outer tube 4 can be securely prevented.

As shown in FIG. 2 (and in FIGS. 3 to 5, as well), the inner tube 7 is disposed inside the outer tube 4. The inner tube 7 is displaceable relative to the outer tube 4, namely, turnable about the axis of the outer tube 4 and movable along the axial direction of the outer tube 4.

The inner tube 7 has a sealing member placing part 73 where to place the first sealing member 6. The sealing member placing part 73 is composed of a pair of annular plate-shaped portions 731 and 732 which are provided on the inside of the inner tube 7 and which grip the first sealing member 6 therebetween from the upper and lower sides.

In addition, the inner tube 7 has a sliding member 74 which slides the hollow needle 5 when the inner tube 7 is displaced, and a fixing part 75 for fixing the sliding member 74. The sliding member 74 is a member which is tubular in shape, has a reduced diameter portion 741 reduced in inside diameter, and is formed of an elastic material. A material constituting the sliding member 74 is not particularly limited. Examples of the material include elastic materials such as various rubber materials such as natural rubber, butyl rubber, isoprene rubber, butadiene rubber, styrene-butadiene rubber, silicone rubber, and etc., various thermal plastic elastomers based on polyurethane, polyester, polyamide, olefin, styrene or the like, and their mixtures and the like. When the inner tube 7 is displaced, the reduced diameter portion 741 slides in contact with an outer circumferential portion 54 of the hollow needle 5. The fixing portion 75 is a tubular portion which is formed to project downward from, and integrally with, the plate-shaped portion 732.

As shown in FIG. 6 (and in FIGS. 7 to 9, as well), the wall portion of the inner tube 7 is projectingly formed with the projected portion 76 at an outer circumferential portion thereof. This projected portion 76 is inserted in the groove portion 48 of the outer tube 4, and is moved within the groove portion 48 attendantly on displacement of the inner tube 7. This ensures that the first connector 2 can assume a first state (the state shown in FIGS. 6 and 7) in which the projected portion 76 is located in the transverse groove 481, a second state (the state shown in FIG. 8) in which the projected portion 76 is located in a crossing part 483 of the transverse groove 481 and the longitudinal groove 482 as a result of an operation of turning of the inner tube 7 relative to the outer tube 4 starting from the first state, and a third state (the state shown in FIG. 9) in which the projected portion 76 is located in the longitudinal groove 482 as a result of an operation of pushing of the inner tube 7 relative to the outer tube 4 starting from the second state.

When the second connector 3 is inserted into the first connector 2 being in the first state shown in FIG. 6 (FIG. 2) (this operation will hereinafter be referred to as "the inserting operation"), a second sealing member 11 of the second connector 3 comes into contact with the first sealing member 6 of the first connector 2, and presses the first sealing member 6 in the proximal direction, attempting to move the first sealing member 6 together with the inner tube 7. Since the projected portion 76 of the inner tube 7 is located in the transverse groove 481 of the outer tube 4, however, the inner tube 7 is restrained from being moved in the proximal direction (see FIGS. 3 and 7).

Figure 7:
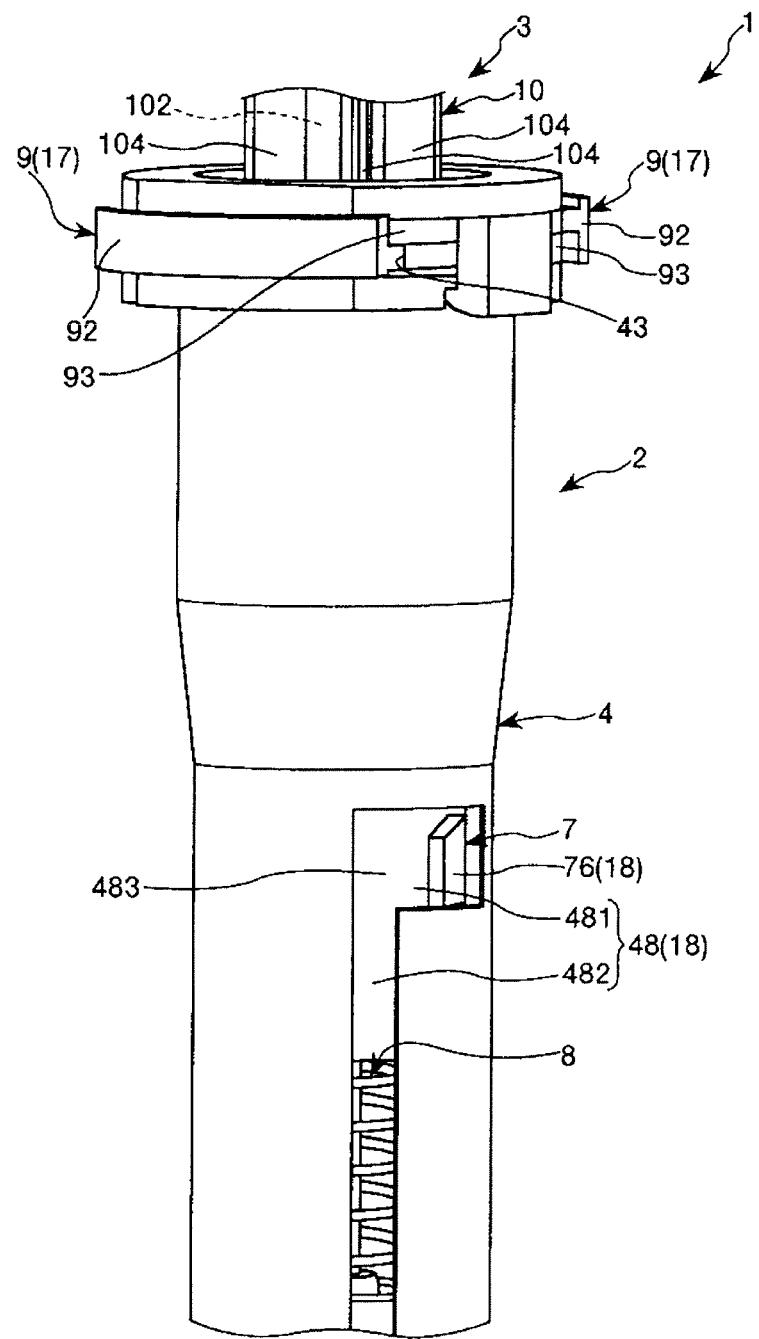
[FIG. 7]
Figure 8:
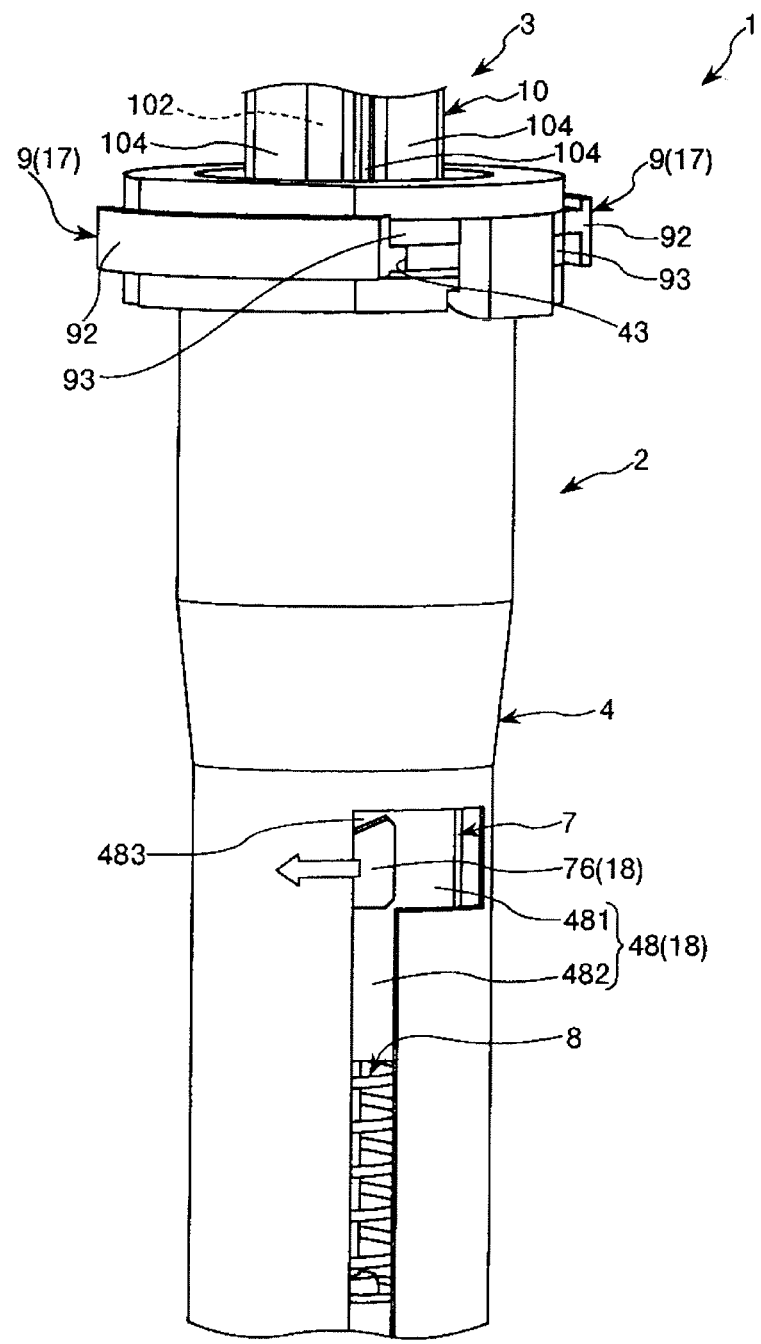
[FIG. 8]

When an operation of rotating the inner tube 7 in the direction of arrow in FIG. 8 by, for example, putting a finger on the projected portion 76 of the inner tube 7 is carried out, starting from the state shown in FIG. 7, the first connector 2 comes into the second state shown in FIG. 8. As a result, the restraint on proximal movement of the inner tube 7 is canceled, to permit the movement, so that the inserting operation can be resumed. Incidentally, as shown in FIG. 4, the close contact between the first sealing member 6 and the second sealing member 11 is maintained even in the second state. In addition, in the second state, the inner tube 7 and the second connector 3 (the second connector body 10) are fixed together by a locking means 19. As a result, close contact between a first to-be-pierced section 61 of the first sealing member 6 and a second to-be-pierced section 111 of the second sealing member 11 is fixed. The locking means 19 will be described later.

Figure 9:
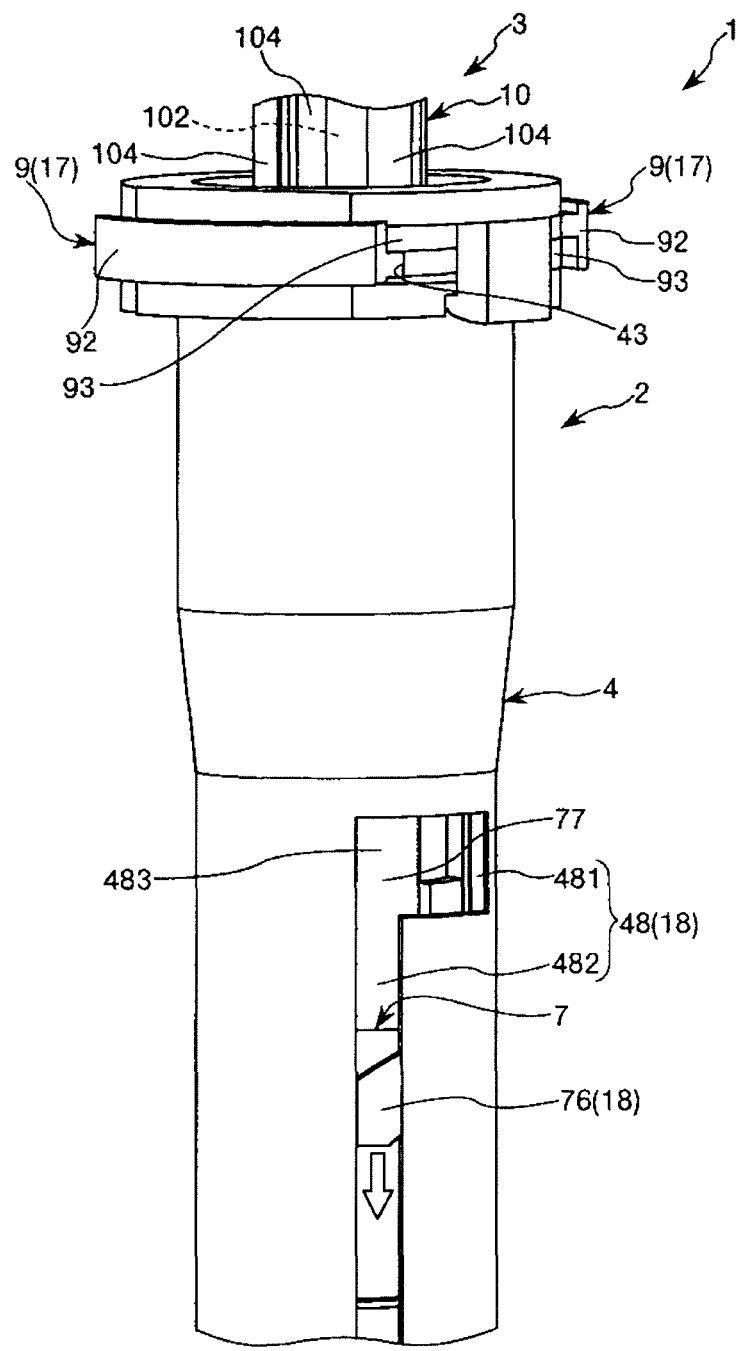
[FIG. 9]

When the second connector 3 is pushed in proximally against the biasing force of the coil spring 8, starting from the state shown in FIG. 8, the inserting operation is resumed, and the first connector 2 comes into the third state shown in FIG. 9. Incidentally, as shown in FIG. 5, the close contact between the first sealing member 6 and the second sealing member 11 is maintained even in the third state.

When the second connector 3 is pulled out of the first connector 2 (this operation will hereinafter be referred to as "the pulling-out operation") in the state shown in FIG. 9 (assembled state), the inner tube 7 is moved distally together with the second connector 3 according to the biasing force of the coil spring 8, reversely to the above-mentioned, and the first connector 2 comes into the second state shown in FIG. 8. In this second state, a further distal movement of the projected portion 76 of the inner tube 7 is restrained. This ensures that the pulling-out operation can be once restrained during its course.

Furthermore, when an operation of rotating the inner tube 7 in a direction reverse to the above-mentioned is carried out starting from the second state, the first connector 2 comes into the first state shown in FIG. 7. As a result, the locking of the inner tube 7 and the second connector 3 by the locking means 9 is canceled, to permit distal movement of the second connector 3 alone, and, accordingly, the pulling-out operation can be resumed. When the pulling-out operation is resumed, the first connector 2 and the second connector 3 are again brought into the disassembled state shown in FIG. 6.

Thus, in the connector assembly 1, the restraint on the inserting operation, the canceling of the restraint on the inserting operation, the restraint on the pulling-out operation, and the canceling of the restraint on the pulling-out operation are performed according to the position of the projected portion 76 of the inner tube 7 within the groove portion 48 of the outer tube 4. Therefore, the projected portion 76 of the inner tube 7 and the groove portion 48 of the outer tube 4 constitute "an operation restricting means 18" by which these operations are restricted.

As shown in FIG. 2, the inner tube 7 is formed at a distal portion thereof with a plurality (in this embodiment, four sheets) of engaging pieces (elastic pieces) 77 projected in the distal direction. Each of the engaging pieces 77 is provided at a distal portion thereof with a claw 771 which can be engaged with a recessed portion (engaging portion) 101a of the second connector 3.

Incidentally, the recessed portion 101a is a portion which is formed at a distal portion of an outer circumferential portion 101 of the second connector body 10, in an annular shape along the circumferential direction.

Each of the engaging pieces 77 is inclined outward in the condition where the second connector 3 is not yet inserted into the first connector 2. This ensures that, in the condition where the second connector 3 is inserted in the first connector 2, each of the engaging pieces 77 can assume a state of being apart from the recessed portion 101a of the second connector 3 (the states shown in FIGS. 3 and 10) and a state of being set close to and engaged with the recessed portion 101a by being pressed by pressing portions 471 of the outer tube 4 (the states shown in FIGS. 4, 5 and 11). By this engagement, the inner tube 7 and the second connector 3 are assuredly locked together.

Incidentally, the pressing portions 471 are composed of a plurality of (in this embodiment, four) ribs formed at the inner circumferential portion 47 of the outer tube 4 along the axial direction of the latter.

In addition, these pressing portions 471 are arranged at regular intervals along the circumferential direction of the outer tube 4. In the state shown in FIG. 10, one sheet of engaging pieces 77 is located between the adjacent pressing portions 471, and the pressing of the pressing portions 471 against the engaging pieces 77 is not yet performed. In this instance, the first connector 2 is in the above-mentioned first state.

The engaging pieces 77 are arranged at regular intervals around the axis of the inner tube 7. With an operation of rotating the inner tube 7 as above-mentioned carried out starting from the state shown in FIG. 10, the engaging pieces 77 are let climb slant surfaces 472 of the pressing portions 471, resulting in that each pressing portion 471 presses each engaging piece 77 against an elastic force of the latter. This causes the four engaging pieces 77 to be evenly engaged along the circumferential direction of the second connector 3, so that the inner tube 7 and the second connector 3 are locked together more assuredly. In this instance, the first connector 2 is in the above-mentioned second state. The state in which the pressing portions 471 are pressing the engaging pieces 77 is maintained even after the first connector 2 is brought into the above-mentioned third state.

Thus, in the connector assembly 1, the engaging pieces 77 of the inner tube 7, the pressing portions 471 of the outer tube 4 and the recessed portion 101a of the second connector 3 constitute "the locking means 19" by which the inner tube 7 and the second connector 3 are locked together in an assured manner. Besides, the locking means 19 operates when the first connector 2 is shifted from the first state into the second state; in other words, the locking means 19 operates interlockedly with a canceling operation of canceling the restraint on the inserting operation. In addition, in a reverse manner, the locking means 19 operates also when the first connector 2 is shifted from the second state into the first state; in other words, the locking means 19 operates also interlockedly with a canceling operation of canceling the restraint on the pulling-out operation. This ensures that, during displacement of the first connector 2 between the first state and the second state, in other words, before and after the piercing by the hollow needle 5 of the first sealing member 6 and the second sealing member 11, the first sealing member 6 and the second sealing member 11 can assuredly be held in close contact with each other, and the second connector 3 can be prevented from being unexpectedly pulled out alone (made to slip off) at the time of the pulling-out operation.

Incidentally, the materials constituting the outer tube 4, the inner tube 7, the gripping and pressing members 9 and the hub 12 are not particularly restricted. Examples of the materials include various resins such as polyvinyl chloride, polyethylene, polypropylene, cyclic polyolefins, polystyrene, poly(4-methylpentene-1), polycarbonate, acrylic resins, acrylonitrile-butadiene-styrene copolymer, polyesters including polyethylene terephthalate, polyethylene naphthalate and the like, butadiene-styrene copolymer, and polyamides (e.g., nylon 6, nylon 6,6, nylon 6,10, nylon 12). Among these materials, such resins as the polypropylene, the cyclic polyolefins and the polyesters are preferred, since they are easy to mold and are low in water vapor permeability.

As shown in FIG. 2, the hollow needle 5 formed of a metallic material is disposed on the axis of the outer tube 4. As above-mentioned, the hollow needle 5 is supported by the hub 12 at a proximal portion thereof.

The hollow needle 5 is tubular in shape, and its lumen functions as the first flow channel 52 which permits a dissolving liquid P (liquid) to pass therethrough. In addition, the hollow needle 5 is closed at the distal end thereof, and is formed with a side hole (opening) 53 opening at a distal portion of the wall portion thereof. The side hole 53 communicates with the first flow channel 52.

The hollow needle 5 is formed at the distal end thereof with a sharp needlepoint 51. As shown in FIG. 5, the needlepoint 51 is capable of piercing the first sealing member 6 of the first connector 2 and the second sealing member 11 of the second connector 3 which will be described later. As shown in FIG. 5, in the assembled state, a portion of the hollow needle 5 which ranges from the needlepoint 51 to the part where the side hole 53 is formed is exposed to the lumen of the second connector 3. This ensures that the lumen of the hollow needle 5 and the lumen of the second connector 3 communicate with each other, in other words, the first flow channel 52 of the first connector 2 and a second flow channel 102 of the second connector 3 (described later) communicate with each other, via the side hole 53 of the hollow needle 5.

As shown in FIG. 2, the first sealing member 6 is disposed inside the inner tube 7. The first sealing member 6 is a member for sealing off the lumen portion of the inner tube 7. The first sealing member 6 is circular disk-like in shape, and is so disposed that a thickness direction thereof coincides with the axial direction of the inner tube 7. This ensures that when the first sealing member 6 is moved toward the proximal side along the axial direction of the hollow needle 5, the first sealing member 6 is pierced by the needlepoint 51 of the hollow needle 5 easily and assuredly.

In addition, the first sealing member 6 is an elastic body the thickness of which is greater in a central portion thereof than in an edge portion thereof. This central portion serves as the first to-be-pierced section 61 to be pierced by the hollow needle 5. Besides, the edge portion of the first sealing member 6 is gripped between the pair of plate-shaped portions 731 and 732 of the inner tube 7, as above-mentioned. This ensures that the first sealing member 6 is fixed to the inner tube 7 assuredly and can be moved together with the inner tube 7.

In addition, in the connector assembly 1, the sum of the sliding resistance between portions of the first sealing member 6 (the first to-be-pierced section 61) and the second sealing member 11 (the second to-be-pierced section 111) pierced by the hollow needle 5 and the outer circumferential portion 54 of the hollow needle 5 making contact with these to-be-pierced sections and the sliding resistance between the reduced diameter portion 741 of the sliding member 74 and the outer circumferential portion 54 of the hollow needle 5 making contact with the reduced diameter portion 741, is set to be smaller than the biasing force of the coil spring 8. This ensures that when the locking of the first connector 2 in the third state shown in FIG. 5 by the stopper 17 is canceled, the first connector 2 can be returned into the second state shown in FIG. 4 by the biasing force of the coil spring 8. Incidentally, the method for setting a magnitude relationship among these forces is not particularly restricted. Examples of the method include methods in which the materials constituting the first sealing member 6, the second sealing member 11 and the sliding member 74 are selected, or the thicknesses of the first to-be-pierced section 61 and the second to-be-pierced section 111 are controlled, or the material constituting the coil spring 8 is selected, or the wire diameter and the number of turns of the coil spring 8 are controlled, or the outside diameter of the hollow needle 5 is controlled.

As shown in FIG. 2, when the first to-be-pierced section 61 is in a natural state wherein no external force is exerted thereon, a distal end face 612 of the first to-be-pierced section 61 is in a protuberant form. In the close contact state wherein the first sealing member 6 and the second sealing member 11 are in close contact with each other, as shown in FIG. 3, the distal end face 612 having been protuberant is collapsed flat. As a result, the close contact state is more assured, and, accordingly, it is possible to secure liquid-tightness at a boundary part between the first sealing member 6 and the second sealing member 11. This ensures that feeding of liquid in the assembled state can be performed safely and reliably.

Incidentally, the material constituting the first sealing member 6 is not specifically restricted; for example, materials the same as or similar to those mentioned above as examples of the material constituting the sliding member 74 can be used.

As shown in FIG. 2, the coil spring 8 formed from a metallic material such as stainless steel is disposed inside the outer tube 4. The coil spring 8, in its compressed state, has its distal end in contact with the plate-shaped portion 732 of the inner tube 7, and has its proximal end in contact with the bottom portion 128 of the hub 12. This makes it possible to bias the hub 12 in the proximal direction assuredly, and to assuredly bias the first sealing member 6 in the distal direction through the inner tube 7. The hollow needle 5 extends through the inside of the coil spring 8. In other words, the coil spring 8 is disposed around the hollow needle 5 along the hollow needle 5. Incidentally, the biasing means is not restricted to the coil spring 8; for example, the biasing means may be composed of a bellows-like leaf spring, or a hollow cylindrical or bellows-like rubber.

As shown in FIGS. 1 and 2, the second connector 3 has the tubular second connector body 10, and the second sealing member 11 provided on the second connector body 10.

The second connector body 10 is a hollow cylindrical member. The lumen of the second connector body 10 functions as the second flow channel 102 which permits liquid to pass therethrough. As shown in FIG. 17, the second connector body 10 has its distal portion (second connection portion) as a bottle needle portion 103 which is tapered off, and is capable of piercing the rubber stopper 505 of the bag 50. In addition, the bottle needle portion 103 is formed with a side hole (not shown). When the bottle needle portion 103 is made to pierce the rubber stopper 505 of the bag 50 and the side hole is exposed to the inside of the bag 50, the inside of the bag 50 and the second flow channel 102 communicate with each other. This ensures that the liquid having passed through the second flow channel 102 can be supplied into the bag 50.

In addition, as above-mentioned, the second connector body 10 is formed at an intermediate portion thereof with the engagement portions 105a and 105b for engagement with the first engagement portion 91 of the first connector 2.

Besides, the second connector body 10 is formed at an outer circumferential portion thereof with a plurality of (in this embodiment, four) ribs 104 along the longitudinal direction thereof. These ribs 104 are arranged at regular intervals along the circumferential direction of the outer circumferential portion of the second connector body 10. This makes it possible to reinforce the second connector body 10.

The second connector body 10 is provided at a distal portion thereof with a sealing member placing part 106 for placing the second sealing member 11. The sealing member placing part 106 is composed of a pair of annular plate-shaped portions 106a and 106b which grip the second sealing member 11 therebetween from the upper and lower sides.

Incidentally, the material constituting the second connector body 10 is not particularly limited; for example, such materials as those set forth in the description of the outer tube 4, the inner tube 7, the gripping and pressing members 9 and the hub 12 of the first connector 2 can be used.

As shown in FIG. 2, the second sealing member 11 is a member for sealing off the lumen portion of the second connector body 10, is circular disk-like in shape, and is so disposed that the thickness direction thereof coincides with the axial direction of the second connector body 10. This ensures that the second sealing member 11 can be pierced, together with the first sealing member 6 being in close contact therewith, by the needlepoint 51 of the hollow needle 5 easily and assuredly.

In addition, the second sealing member 11 is an elastic body the thickness of which is greater in a central portion thereof than in an edge portion thereof. The central portion serves as the second to-be-pierced section 111 to be pierced by the hollow needle 5. Besides, the edge portion of the second sealing member 11 is gripped between the pair of plate-shaped portions 106a and 106b of the second connector body 10 as described above. This ensures that the second sealing member 11 is fixed to the second connector body 10 assuredly.

As shown in FIG. 2, the second to-be-pierced section 111, in a natural state wherein no external force is exerted thereon, has its proximal end face 112 in a protuberant form. Besides, in a close contact state wherein the first sealing member 6 and the second sealing member 11 are in close contact with each other, as shown in FIG. 3, the proximal end face 112 having been protuberant is collapsed flat, like the distal end face 612 of the first sealing member 6. This makes the close contact state more assured, so that it is possible to secure liquid-tightness at the boundary part between the first sealing member 6 and the second sealing member 11.

Incidentally, the material constituting the second sealing member 11 is not specifically restricted; for example, materials the same as or similar to those mentioned above as examples of the material constituting the sliding member 74 can be used.

Now, operating conditions at the time of using the connector assembly 1 will be described below.

[1] Process from disassembled state to assembled state (After mounting of the first connector 2 to the syringe 20, see the drawings in the order of FIG. 2 (FIG. 6)→FIG. 3 (FIG. 7)→FIG. 4 (FIG. 8)→FIG. 5 (FIG. 9))

First, the syringe 20 is mounted to the first connector 2, and the second connector 3 is attached to the bag 50.

As shown in FIG. 12, the hub 12 of the first connector 2 is positioned in a first position by the biasing force (elastic force) of the coil spring 8.

At the time of mounting the syringe 20 to the first connector 2, the mouth portion 202 of the syringe 20 is inserted into a proximal portion of the hub portion 122 of the hub 12 of the first connector 2, and the hub 12 is moved in the distal direction against the biasing force of the coil spring 8, to bring the hub 12 into a second position, as shown in FIG. 13. As a result, rotation in the direction for tightening the screw engagement of the hub 12 is inhibited. Then, the lock adapter 203 is rotated together with the syringe 20, to bring the lock adapter 203 into screw engagement with the projection 123 of the hub portion 122. As a result, the hub portion 122 and the mouth portion 202 of the syringe 20 are connected to each other, and the projection 123 and the lock adapter 203 are put into screw engagement with each other, whereby the syringe 20 is held on the hub 12. Incidentally, the hub 12 is moved into the first position by the biasing force of the coil spring 8.

As above-mentioned, after the mounting of the syringe 20 onto the hub portion 122, the syringe 20 cannot be detached from the hub portion 122 even if the hub 12 is positioned either in the first position or in the second position. This makes it possible to prevent the syringe 20 from being unintentionally disengaged from the hub portion 122. Particularly, it is ensured that a drug dangerous when erroneously touched by a medical care staff, such as a carcinostatic agent or an immunosuppressant, can be prevented from being deposited on the medical care staff.

In addition, when the hub portion 122 is positioned in the first position, the hub 12 is capable of both forward rotation and reverse rotation. Therefore, by rotating the syringe 20 together with the hub 12 in the condition where the syringe 20 is mounted to the hub portion 122, graduations provided on the syringe 20 can be easily looked at.

Next, as shown in FIG. 2, the second connector 3 in the disassembled state is brought, its proximal end first, toward a distal portion of the first connector 2. In the disassembled state, the first connector 2 is in the first state (the state wherein the projected portion 76 of the inner tube 7 is positioned in the transverse groove 481 of the groove portion 48 of the outer tube 4) (see FIG. 6). In addition, the first sealing member 6 is located on the distal side relative to the hollow needle 5.

When the second connector 3 is gradually inserted into the first connector 2, as shown in FIGS. 3 and 7, the distal end face 612 of the first sealing member 6 of the first connector 2 and the proximal end face 112 of the second sealing member 11 of the second connector 3 are first put into contact with each other, to make close contact with each other through elastic deformation. In this instance, the first connector 2 is in the first state (see FIG. 7), as above-mentioned, the operation of inserting the second connector 3 into the first connector 2 is therefore once restrained.

In addition, as shown in FIG. 3, the stopper 17 operates (the gripping and pressing members 9 of the first connector 2 are engaged with the engagement portion 105a of the second connector 3), to prevent the second connector 3 from being again returned in the distal direction to be disengaged from the first connector 2.

Next, when an operation of rotating the inner tube 7 of the first connector 2 in the direction of arrow in FIG. 8 is conducted, as shown in FIG. 8, the first connector 2 is put into the second state (the state wherein the projected portion 76 of the inner tube 7 is positioned in the crossing part 483 of the groove portion 48 of the outer tube 4). This results in that the restraint on the inserting operation is canceled, as above-mentioned, so that the inserting operation can be resumed.

Besides, the assembled state of the first connector 2 and the second connector 3 is maintained by the stopper 17 and the locking means 19. This ensures that pulling-out of the second connector 3 from the first connector 2, in other words, unintentional disassembly of the connector assembly 1 being in the assembled state, can be prevented securely. Consequently, the dissolving liquid P can be transported safely, via the connector assembly 1.

In addition, in the assembled state, close contact between the first sealing member 6 of the first connector 2 and the second sealing member 11 of the second connector 3 is maintained (see FIG. 5). This makes it possible to securely maintain the liquid-tightness (air-tightness) of the first flow channel 52 and the second flow channel 102, particularly in the vicinity of the joint part of these flow channels. Accordingly, the dissolving liquid P passing through these flow channels is securely prevented from leaking out of the connector assembly 1 which is in the assembled state.

Besides, in the state shown in FIG. 5, a proximal end 78 of the inner tube 7 makes contact with a distal end 129 of the hub 12. This restricts the limit of insertion of the second connector 3.

[2] Process from assembled state into disassembled state again (See the drawings in the order of FIG. 5 (FIG. 9)→FIG. 4 (FIG. 8)→FIG. 3 (FIG. 7)→FIG. 2 (FIG. 6))

The gripping and pressing members 9 are operated, starting from the states shown in FIGS. 5 and 9, to cancel the locked state between the first connector 2 and the second connector 3. This makes it possible to start a pulling-out operation of pulling the second connector 3 out of the first connector 2.

When the pulling-out operation is started, as shown in FIGS. 4 and 8, the second connector 3 is moved in the distal direction, reversely to the above-mentioned. In this instance, the biasing force of the coil spring 8 is acting on the first sealing member 6 through the inner tube 7, so that the first sealing member 6 can follow up to the movement of the second connector 3. This ensures that the close contact between the first sealing member 6 and the second sealing member 11 is maintained even during the pulling-out operation.

When the first connector 2 is put into the second state, the pulling-out operation is once restrained as above-mentioned (see FIG. 8). In this instance, as shown in FIG. 4, the side hole 53 of the hollow needle 5 is located on the proximal side relative to the second sealing member 11 (in the configuration shown, the first sealing member 6 located on the more proximal side than the second sealing member 11). Incidentally, those parts of the first sealing member 6 and the second sealing member 11 which have been pierced by the hollow needle 5 are closed by self-closing properties of the sealing members.

Subsequently, an operation of rotating the inner tube 7 in the direction reverse to the above-mentioned, whereon the first connector 2 is put into the first state shown in FIG. 7. In this instance, as shown in FIG. 3, the locking of the inner tube 7 and the second connector 3 by the locking means 19 is canceled, and distal movement of only the second connector 3 is permitted. As a result, the operation of pulling out the second connector 3 can be resumed.

When the pulling-out operation is resumed, as shown in FIGS. 2 and 6, the first to-be-pierced section 61 and the second to-be-pierced section 111 having been in close contact with each other are spaced apart from each other, so that the connector assembly 1 having been in the assembled state can again be put into the disassembled state. Thereafter, it is possible to detach the first connector 2 from the syringe 20, and to administer a liquid medicine from the syringe 20.

Thus, in the connector assembly 1, at the time of pulling the second connector 3 out of the first connector 2, the first sealing member 6 and the second sealing member 11 can be prevented from being spaced away from each other before the hollow needle 5 has completely pulled out of the second sealing member 11. This ensures that the liquid-tightness of the first flow channel 52 and the second flow channel 102 can be maintained even during disassembling of the connector assembly 1 being in the assembled state. Therefore, the liquid medicine (liquid) in these flow channels is securely prevented from leaking out of the connector assembly 1. Consequently, feeding of the liquid medicine can be safely carried out using the connector assembly 1.

While the connector and the connector assembly according to the present invention has been described above while referring to the embodiment shown in the drawings, the invention is not restricted to the embodiment. The components of the connector and of the connector assembly can each be replaced by one of an arbitrary which can exhibit a function equivalent to the original function. Besides, arbitrary structures may be added.

In addition, while the engagement-disengagement mechanism is composed of the ratchet teeth formed at the inner circumferential portion of the outer tube and the pawls formed on the flange of the hub, this structure is not restrictive. For example, the engagement-disengagement mechanism may be composed of pawls formed at the inner circumferential portion of the outer tube and ratchet teeth formed on the flange of the hub.

Besides, while the operation restricting means is composed of the groove portion formed in the wall portion of the outer tube and the projected portion which is projectingly formed at the wall portion of the inner tube and is inserted in the groove portion, this is not restrictive. For example, the operation restricting means may be composed of a groove portion formed in the wall portion of the inner tube and a projected portion which is projectingly formed at the wall portion of the outer tube and is inserted in the groove portion.

In addition, while the first to-be-pierced section and the second to-be-pierced section have their end faces protuberant, this is not restrictive. For example, a configuration may be adopted wherein only the end face of one of the to-be-pierced sections is protuberant.

Besides, in the present invention, a configuration in which the coil spring 8 is absent may also be adopted.

Industrial Applicability

According to the present invention, the connector is provided with the engagement-disengagement mechanism, so that the medical instrument connected to the connector would not easily be disengaged.

In addition, the engagement-disengagement mechanism enables the medical instrument to be rotated relative to the connector in the state of being connected to the connector. This ensures that graduations provided on the medical instrument can be easily observed during an operation of dissolving a medicine in the dissolving liquid. Accordingly, the present invention has industrial applicability.

What is claimed is:

1. A connector comprising:
   an outer tube;
   a hub disposed at a proximal portion of the outer tube so as to be movable in a direction of an axis of the outer tube and rotatable about the axis of the outer tube, relative to the outer tube, wherein the hub has a connection portion that is connectable on a proximal side of the hub to a medical instrument having a screw engagement part, the hub has a projected portion for screw engagement with the screw engagement part of the medical instrument, and at least a distal portion of the hub that is insertable in the outer tube;
   an engagement-disengagement mechanism provided at a joint part between the outer tube and the hub, wherein the engagement-disengagement mechanism permits rotation of the hub in both of a forward direction and a reverse direction when the hub is positioned in a first position, and inhibits the rotation of the hub in only one of the forward direction and the reverse direction when the hub is positioned in a second position on a distal side relative to the first position; and
   an elastically resilient member for biasing the hub in a proximal direction disposed within the outer tube at a distal side of the hub, wherein the hub is positioned in the first position by a biasing force of the elastically resilient member
   wherein the elastically resilient member expands to push the hub proximally towards the first position.

2. The connector according to claim 1, wherein a rotating direction of the hub for tightening the screw engagement between the projected portion of the hub and the screw engagement part of the medical instrument coincides with a direction in which the rotation of the hub is inhibited by the engagement-disengagement mechanism.

3. The connector according to claim 1,
   wherein the hub has a flange at an outer circumferential portion thereof, and
   the engagement-disengagement mechanism has pawls provided on one of the flange and an inner circumferential portion of the outer tube, and ratchet teeth provided on the other of the flange and the inner circumferential portion of the outer tube.

4. The connector according to claim 1,
   wherein when the hub is moved in a distal direction from the first position against the biasing force of the elastically resilient member to be positioned in the second position, the rotation of the hub in only one of the forward direction and the reverse direction is inhibited by the engagement-disengagement mechanism.

5. A connector assembly comprising:
the connector according to claim 1; and
a mating connector connected to the connector and having on a distal side a connection portion to which to connect a liquid storing vessel capable of storing a liquid.

* * * * *